US 7,005,439 B2

(12) United States Patent
Eriksson et al.

(10) Patent No.: US 7,005,439 B2
(45) Date of Patent: *Feb. 28, 2006

(54) COMPOUNDS

(75) Inventors: Tomas Eriksson, Lund (SE); Krister Henriksson, Lund (SE)

(73) Assignee: AstraZeneca AB, Södertälje (SE)

( * ) Notice: Subject to any disclaimer, the term of this patent is extended or adjusted under 35 U.S.C. 154(b) by 0 days.

This patent is subject to a terminal disclaimer.

(21) Appl. No.: 10/311,667

(22) PCT Filed: Jun. 14, 2001

(86) PCT No.: PCT/SE01/01378

§ 371 (c)(1),
(2), (4) Date: Dec. 17, 2002

(87) PCT Pub. No.: WO01/98272

PCT Pub. Date: Dec. 27, 2001

(65) Prior Publication Data

US 2003/0153555 A1 Aug. 14, 2003

(30) Foreign Application Priority Data

Jun. 20, 2000 (SE) ............................................ 0002330
Oct. 31, 2000 (SE) ............................................ 0003980

(51) Int. Cl.
*A61K 31/445* (2006.01)
*C07D 401/06* (2006.01)

(52) U.S. Cl. ........................ 514/326; 514/317; 514/318; 514/319; 514/331; 514/424; 514/426; 546/205; 546/207; 546/216; 546/229; 548/512; 548/544; 548/557; 548/578

(58) Field of Classification Search ................ 514/317, 514/318, 319, 326, 331, 424, 426; 546/205, 546/207, 216, 229; 548/512, 544, 557, 578
See application file for complete search history.

(56) References Cited

U.S. PATENT DOCUMENTS

| 3,203,992 | A | 8/1965 | Kunz et al. .................. 564/351 |
| 3,577,432 | A | 5/1971 | Helsley ........................ 548/538 |
| 3,755,584 | A | 8/1973 | Plotnikoff et al. ............. 514/292 |
| 3,818,017 | A | 6/1974 | Janssen et al. ................ 546/199 |
| 3,894,030 | A | 7/1975 | Janssen et al. ................ 546/199 |
| 4,029,801 | A | 6/1977 | Cavalla et al. ................ 514/329 |
| 4,166,119 | A | 8/1979 | Effland et al. ................ 514/278 |
| 4,264,613 | A | 4/1981 | Regnier et al. ............... 514/322 |
| 4,338,323 | A | 7/1982 | Regnier et al. ............... 514/318 |
| 5,576,321 | A | 11/1996 | Krushinski, Jr. et al. ............................. 514/254.09 |
| 5,614,523 | A | 3/1997 | Audia et al. ................ 514/254.08 |
| 5,614,533 | A | 3/1997 | Anderson et al. ............ 514/314 |
| 5,627,196 | A | 5/1997 | Audia et al. ................. 514/323 |
| 5,741,789 | A | 4/1998 | Hibschman et al. ....... 514/212.02 |
| 5,789,402 | A | 8/1998 | Audia et al. ............... 514/212.02 |

FOREIGN PATENT DOCUMENTS

| DE | 37 23 568 | 1/1989 |
| DE | 37 23 648 | 1/1989 |
| DE | 197 03 131 A1 | 7/1998 |
| DE | 197 55 268 | 6/1999 |
| EP | 0 095 454 A2 | 11/1983 |
| EP | 0 128 007 A2 | 12/1984 |
| EP | 0 496 691 A1 | 7/1992 |
| EP | 0 587 311 A1 | 3/1994 |
| EP | 0 722 941 A2 | 7/1996 |
| EP | 0 903 349 A2 | 3/1999 |
| FR | 2.190.430 | 6/1972 |
| GB | 1368012 | 9/1974 |
| WO | WO 93/25528 | 12/1993 |
| WO | WO 97/23458 | 7/1997 |
| WO | WO 98/32442 | 7/1998 |
| WO | WO 99/25686 | 5/1999 |
| WO | WO 99/31092 | 6/1999 |
| WO | WO 99/65895 | 12/1999 |
| WO | WO 00/35449 | 6/2000 |
| WO | WO 00/53600 | 9/2000 |
| WO | WO 00/58305 | 10/2000 |
| WO | WO 00/69820 | 11/2000 |
| WO | WO 01/14333 A1 | 3/2001 |
| WO | WO 01/43744 | 6/2001 |
| WO | WO 01/44227 | 6/2001 |
| WO | WO 01/87839 A1 | 11/2001 |

OTHER PUBLICATIONS

Friebe et al. "Piperidinopropyl derivatives . . . " Ca 94:103172 (1981).*
Meurer et al. "Discovery of potent human CCR5 antagonists for the . . . " CA 2000:331722 (2000).*
Cohen et al. "Cytokine function . . . " CA 125:31527 (1996).*
U.S. Appl. No. 10/204,754, filed Aug. 23, 2002, Hansen et al.
U.S. Appl. No. 10/204,789, filed Aug. 23, 2002, Hansen et al.
U.S. Appl. No. 10/204,790, filed Aug. 23, 2002, Bodkin et al.
U.S. Appl. No. 10/311,841, filed Dec. 17, 2002, Eriksson et al.
U.S. Appl. No. 10/468,179, filed Aug. 18, 2003, Brough et al.
U.S. Appl. No. 10/472,017, filed Sep. 19, 2003, Eriksson et al.
U.S. Appl. No. 10/472,412, filed Sep. 16, 2003, Eriksson et al.

(Continued)

*Primary Examiner*—Celia Chang
(74) *Attorney, Agent, or Firm*—Fish & Richardson P.C.

(57) ABSTRACT

The invention provides compounds of general formula (I) wherein m, n, $Z^1$, $Z^2$, $R^1$, $R^2$, $R^3$, $R^4$, $R^5$, $R^6$, $R^7$ and $R^8$ are as defined in the specification, process for their preparation, pharmaceutical compositions containing them and their use in therapy.

11 Claims, No Drawings

OTHER PUBLICATIONS

Archibald et al., "Antiinflammatory 4–acylaminopiperidines", *CAPLUS* 77:34355 (1972).

Leclerc et al., "Derivatives Related to Betaxolol with α–and β–Adrenergic Activities", *Arzneim.–Forsch/Drug. Res.* 35(11):1357–1367 (1985).

Rubini et al., "Synthesis of Isosteric Methylene–Oxy Pseudodipeptide Analogues as Novel Amide Bond Surrogate Units", *Tetrahedron* 42(21):6039–6045 (1986).

Timmermans et al., "Hypotensive Properties of Benzodioxane Derivatives Structurally Related to R 28935. Comparison of Activity with some Receptor Affinities", *Arch. int. Pharmacodyn.* 255:321–334 (1982).

U.S. Appl. No. 10/204,790, filed Aug. 23, 2002, Bodkin et al.

U.S. Appl. No. 10/204,789, filed Jul. 31, 2002, Hansen et al.

U.S. Appl. No. 10/204,754, filed Aug. 23, 2002, Hansen et al.

U.S. Appl. No. 10/311,841, filed Dec. 17, 2002, Eriksson.

U.S. Appl. No. 10/471,499, filed Sep. 11, 2003, Brough et al.

U.S. Appl. No. 10/472,017, filed Sep. 19, 2003, Eriksson et al.

Marc Payard et al., "N–Aminomethylated Derivatives of Some Hydroxamic Acids as Anti–Inflammatories," Eur. J. Med. Chem., pp. 1–10 (Jan. 21, 1975).

Frank Navas III, et al., "The Design and Synthesis of a Hapten for 1192U90, a Potential Atypical Antipsychotic Agent," Synthetic Communications, vol. 26, No. 7, pp. 1411–1421 (1996).

Jon L. Wright et al., "Discovery of Selective Dopamine D4 Receptor Antagonists: 1–Aryloxy–3–(4–Aryloxypiperdinyl)–2–Propanols", vol. 7, No. 11, Bioorganic & Medicinal Chemistry Letters, 1377–1380 (1997).

STN International, File CAPLUS, CAPLUS Accession No. 1968.402884.

Joseph Hesselgesser, et al., "Identification and Characterization of Small Molecule Functional Antagonists of the CCR1 Chemokine Receptor," The Journal of Biological Chemistry, vol. 273, No. 25, pp. 15687–15692 (1998).

O.M. Zack Howard, et al., "Chemokines: progress toward identifying molecular targets for therapeutic agents," Trends in Biotechnology, vol. 14, pp. 46–51 (1996).

Tomoaki Komai, et al., "Structure–Activity Relationships of HIV–1 PR Inhibitors Containg AHPBA–II. Modification of Pyrrolidine Ring at P1' Proline," Bioorganic & Medicinal Chemistry, vol. 4, No. 8, pp. 1365–1933 (1996).

Manabu Hori, Kim D. Janda, "A Soluble Polymer Approach to the "Fishing Out" Principle: Synthesis and Purification of β–Amino Alcohols," J. Org. Chem, vol. 63, pp. 889–894 (1998).

Christopher J. Cattanach et al., "Studies in the Indole Series. Part IV. Tetrahydro–5H–pyrido[4, 3–b]indoles as serotonin antagonists," J. Chem. Soc. C., vol. 10, p. 1235–1243 (1968).

* cited by examiner

COMPOUNDS

CROSS REFERENCE TO RELATED APPLICATIONS

The present application is a national phase application under 35 U.S.C. Section 371 filed from International Patent Application PCT/SE01/01378, filed 14 Jun. 2001, which claims priority to Swedish patent application Ser. No. 0002330-9, filed 20 Jun. 2000 and Swedish patent application Ser. No. 0003980-0, filed 31 Oct. 2000. The contents of these applications are incorporated herein by reference in their entirety.

The present invention relates to novel compounds, processes for their preparation, pharmaceutical compositions containing them and their use in therapy.

Chemokines play an important role in immune and inflammatory responses in various diseases and disorders, including asthma and allergic diseases, as well as autoimmune pathologies such as rheumatoid arthritis and atherosclerosis. These small secreted molecules are a growing superfamily of 8–14 kDa proteins characterised by a conserved four cysteine motif. The chemokine superfamily pan be divided into two main groups exhibiting characteristic structural motifs, the Cys-X-Cys (C-X-C) and Cys-Cys (C-C) families. These are distinguished on the basis of a single amino acid insertion between the NH-proximal pair of cysteine residues and sequence similarity.

The C-X-C chemokines include several potent chemoattractants and activators of neutrophils such as interleukin-8 (IL-8) and neutrophil-activating peptide 2 (NAP-2).

The C-C chemokines include potent chemoattractants of monocytes and lymphocytes but not neutrophils such as human monocyte chemotactic proteins 1–3 (MCP-1, MCP-2 and MCP-3), RANTES (Regulated on Activation, Normal T Expressed and Secreted), eotaxin and the macrophage inflammatory proteins 1α and 1β (MIP-1α and MIP-1β).

Studies have demonstrated that the actions of the chemokines are mediated by subfamilies of G protein-coupled receptors, among which are the receptors designated CCR1, CCR2, CCR2A, CCR2B, CCR3, CCR4, CCR5, CCR6, CCR7, CCR8, CCR9, CCR10, CXCR1, CXCR2, CXCR3 and CXCR4. These receptors represent good targets for drug development since agents which modulate these receptors would be useful in the treatment of disorders and diseases such as those mentioned above.

In accordance with the present invention, there is therefore provided a compound of general formula

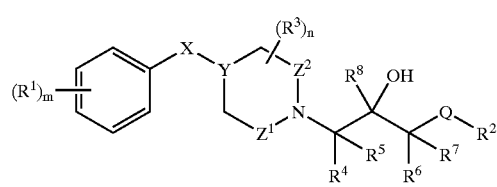

(I)

wherein:

m is 0, 1, 2 or 3;

each $R^1$ independently represents halogen, cyano, nitro, carboxyl, hydroxyl, $C_3$–$C_6$ cycloalkyl, $C_1$–$C_6$ alkoxy, $C_1$–$C_6$ alkoxycarbonyl, $C_1$–$C_6$ haloalkyl, $C_1$–$C_6$ haloalkoxy, —$NR^9R^{10}$, $C_3$–$C_6$ cycloalkylamino, $C_1$–$C_6$ alkylthio, $C_1$–$C_6$ alkylcarbonyl, $C_1$–$C_6$ alkylcarbonylamino, sulphonamido (—$SO_2NH_2$), $C_1$–$C_6$ alkylsulphonyl, —$C(O)NR^{11}R^{12}$, —$NR^{13}C(O)$—$(NH)_pR^{14}$, phenyl, or $C_1$–$C_6$ alkyl optionally substituted by carboxyl or $C_1$–$C_6$ alkoxycarbonyl;

p is 0 or 1;

X represents an oxygen atom or a $CH_2$, $OCH_2$, $CH_2O$, $CH_2NH$, NH, carbonyl or sulphonyl group and Y represents a nitrogen atom or a CH or C(OH) group, provided that when X represents an oxygen atom or a $CH_2O$, $CH_2NH$ or NH group, then Y represents a CH group;

$Z^1$ represents a bond or a group $(CH_2)_q$ where q is 1 or 2;

$Z^2$ represents a bond or a group $CH_2$, with the proviso that $Z^1$ and $Z^2$ do not both simultaneously represent a bond;

Q represents an oxygen or sulphur atom or a group $CH_2$ or NH;

$R^2$ represents a group

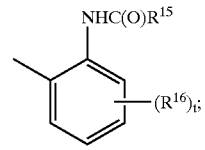

n is 0, 1 or 2;

each $R^3$ independently represents a $C_1$–$C_6$ alkyl, $C_1$–$C_6$ alkoxycarbonyl, —$CH_2OH$ or carboxyl group;

$R^4$, $R^5$, $R^6$ and $R^7$ each independently represent a hydrogen atom or a $C_1$–$C_6$ alkyl group, or $R^4$, $R^5$, $R^6$ and $R^7$ together represent a $C_1$–$C_4$ alkylene chain linking the two carbon atoms to which they are attached to form a 4- to 7-membered saturated carbocycle, or $R^5$, $R^6$ and $R^7$ each represent a hydrogen atom and $R^4$ and $R^8$ together with the carbon atoms to which they are attached form a 5- to 6-membered saturated carbocycle;

$R^8$ represents a hydrogen atom, a $C_1$–$C_6$ alkyl group or is linked to $R^4$ as defined above;

$R^9$ and $R^{10}$ each independently represent a hydrogen atom or a $C_1$–$C_6$ alkyl group, or $R^9$ and $R^{10}$ together with the nitrogen atom to which they are attached form a 4- to 7-membered saturated heterocycle;

$R^{11}$ and $R^{12}$ each independently represent a hydrogen atom or a $C_1$–$C_6$ alkyl group optionally substituted by $C_1$–$C_6$ alkoxycarbonyl;

$R^{13}$ represents a hydrogen atom or a $C_1$–$C_6$ alkyl group;

$R^{14}$ represents a hydrogen atom, or a $C_1$–$C_6$ alkyl group optionally substituted by carboxyl, $C_1$–$C_6$ alkoxy or $C_1$–$C_6$ alkoxycarbonyl;

$R^{15}$ represents a group $C_2$–$C_6$ alkyl, $C_2$–$C_6$ alkenyl, $C_3$–$C_6$ cycloalkyl, $C_5$–$C_6$ cycloalkenyl, adamantyl, phenyl or a saturated or unsaturated 5- to 10-membered heterocyclic ring system comprising at least one heteroatom selected from nitrogen, oxygen and sulphur, wherein each group may be optionally substituted by one or more substituents independently selected from nitro, hydroxyl, oxo, halogen, carboxyl, $C_1$–$C_6$ alkyl, $C_1$–$C_6$ alkoxy, $C_1$–$C_6$ alkylthio, $C_1$–$C_6$ alkylcarbonyl, $C_1$–$C_6$ alkoxycarbonyl, phenyl and —NHC(O)—$R^{17}$, with the proviso that $R^{15}$ does not represent an unsubstituted 1-pyrrolidinyl, an unsubstituted 1-piperidinyl or an unsubstituted 1-hexamethyleneiminyl (1-homopiperidinyl) group;

t is 0, 1, 2 or 3;

each $R^{16}$ independently represents halogen, cyano, nitro, carboxyl, hydroxyl, $C_3$–$C_6$ cycloalkyl, $C_1$–$C_6$ alkoxy, $C_1$–$C_6$ alkoxycarbonyl, $C_1$–$C_6$ haloalkyl, $C_1$–$C_6$ haloalkoxy, —$NR^{18}R^{19}$, $C_3$–$C_6$ cycloalkylamino, $C_1$–$C_6$ alkylthio, $C_1$–$C_6$ alkylcarbonyl, $C_1$–$C_6$ alkylcarbonylamino, sulphonamido (—$SO_2NH_2$), $C_1$–$C_6$ alkylsulphonyl, —$C(O)NR^{20}R^{21}$, —$NR^{22}C(O)$(NH)$_v$$R^{23}$, phenyl, or $C_1$–$C_6$ alkyl optionally substituted by carboxyl or $C_1$–$C_6$ alkoxycarbonyl;

$R^{17}$ represents a $C_1$–$C_6$ alkyl, amino (—$NH_2$) or phenyl group;

$R^{18}$ and $R^{19}$ each independently represent a hydrogen atom or a $C_1$–$C_6$ alkyl group, or $R^{18}$ and $R^{19}$ together with the nitrogen atom to which they are attached form a 4- to 7-membered saturated heterocycle;

$R^{20}$ and $R^{21}$ each independently represent a hydrogen atom or a $C_1$–$C_6$ alkyl group optionally substituted by $C_1$–$C_6$ alkoxycarbonyl;

v is 0 or 1;

$R^{22}$ represents a hydrogen atom or a $C_1$–$C_6$ alkyl group; and $R^{23}$ represents a hydrogen atom, or a $C_1$–$C_6$ alkyl group optionally substituted by carboxyl, $C_1$–$C_6$ alkoxy or $C_1$–$C_6$ alkoxycarbonyl; or a pharmaceutically acceptable salt or solvate thereof.

In the context of the present specification, an alkyl or alkenyl substituent group or an alkyl or alkenyl moiety in a substituent group may be linear or branched. In the definition of $R^{15}$, it should be noted that the unsaturated 5- to 10-membered heterocyclic ring system may be aliphatic or aromatic.

The integer m is preferably 1 or 2.

Each $R^1$ independently represents halogen (e.g. chlorine, fluorine, bromine or iodine), cyano, nitro, carboxyl, hydroxyl, $C_3$–$C_6$ cycloalkyl (cyclopropyl, cyclobutyl, cyclopentyl or cyclohexyl), $C_1$–$C_6$, preferably $C_1$–$C_4$, alkoxy (e.g. methoxy, ethoxy, n-propoxy or n-butoxy), $C_1$–$C_6$, preferably $C_1$–$C_4$, alkoxycarbonyl (e.g. methoxycarbonyl or ethoxycarbonyl), $C_1$–$C_6$, preferably $C_1$–$C_4$, haloalkyl (e.g. trifluoromethyl), $C_1$–$C_6$, preferably $C_1$–$C_4$, haloalkoxy (e.g. trifluoromethoxy), —$NR^9R^{10}$, $C_3$–$C_6$ cycloalkylamino (e.g. cyclopropylamino, cyclobutylamino, cyclopentylamino or cyclohexylamino), $C_1$–$C_6$, preferably $C_1$–$C_4$, alkylthio (e.g. methylthio or ethylthio), $C_1$–$C_6$, preferably $C_1$–$C_4$, alkylcarbonyl (e.g. methylcarbonyl, ethylcarbonyl, n-propylcarbonyl, isopropylcarbonyl, n-butylcarbonyl, n-pentylcarbonyl or n-hexylcarbonyl), $C_1$–$C_6$, preferably $C_1$–$C_4$, alkylcarbonylamino (e.g. methylcarbonylamino or ethylcarbonylamino), sulphonamido, $C_1$–$C_6$, preferably $C_1$–$C_4$, alkylsulphonyl (e.g. methylsulphonyl, ethylsulphonyl, n-propylsulphonyl, isopropylsulphonyl, n-butylsulphonyl, n-pentylsulphonyl or n-hexylsulphonyl), —$C(O)NR^{11}R^{12}$, —$NR^{13}C(O)$—(NH)$_p$$R^{14}$, phenyl, or $C_1$–$C_6$, preferably $C_1$–$C_4$, alkyl (e.g. methyl, ethyl, n-propyl, isopropyl, n-butyl, isobutyl, tert-butyl, n-pentyl or n-hexyl) optionally substituted by carboxyl or $C_1$–$C_6$, preferably $C_1$–$C_4$, alkoxycarbonyl (e.g. methoxycarbonyl or ethoxycarbonyl).

Most preferably, each $R^1$ independently represents halogen (particularly chlorine or fluorine), cyano, nitro, $C_1$–$C_6$ alkoxy (especially methoxy), $C_1$–$C_6$ alkylcarbonyl (especially methylcarbonyl) or $C_1$–$C_6$ alkylcarbonylamino (particularly methylcarbonylamino). Each $R^1$ especially represents halogen or cyano.

Preferably X represents an oxygen atom or a $CH_2$ or NH group.

Preferred combinations of Y, $Z^1$ and $Z^2$ include:

| Y | $Z^1$ | $Z^2$ |
|---|---|---|
| CH | $CH_2$ | bond |
| CH | bond | $CH_2$ |
| CH | $CH_2$ | $CH_2$ |
| CH | $(CH_2)_2$ | bond |
| N | $CH_2$ | $CH_2$ |

Q preferably represents an oxygen atom.

Each $R^3$ independently represents a $C_1$–$C_6$, preferably $C_1$–$C_4$, alkyl (e.g. methyl, ethyl, n-propyl, isopropyl, n-butyl, isobutyl, tert-butyl, n-pentyl or n-hexyl), $C_1$–$C_6$, preferably $C_1$–$C_4$, alkoxycarbonyl (e.g. methoxycarbonyl or ethoxycarbonyl), —$CH_2OH$ or carboxyl group. It is preferred that $R^3$ represents a methyl, methoxycarbonyl, ethoxycarbonyl, —$CH_2OH$ or carboxyl group.

$R^4$, $R^5$, $R^6$ and $R^7$ each independently represent a hydrogen atom or a $C_1$–$C_6$, preferably $C_1$–$C_4$, alkyl (e.g. methyl, ethyl, n-propyl, isopropyl, n-butyl, isobutyl, tert-butyl, n-pentyl or n-hexyl), or $R^4$, $R^5$, $R^6$ and $R^7$ together represent a $C_1$–$C_4$ alkylene chain linking the two carbon atoms to which they are attached to form a 4- to 7-membered saturated carbocycle (e.g. cyclohexyl or preferably cyclopentyl), or $R^5$, $R^6$ and $R^7$ each represent a hydrogen atom and $R^4$ and $R^8$ together with the carbon atoms to which they are attached form a 5- to 6-membered saturated carbocycle (preferably cyclopentyl).

$R^8$ represents a hydrogen atom, a $C_1$–$C_6$, preferably $C_1$–$C_4$, alkyl group (e.g. methyl, ethyl, n-propyl, isopropyl, n-butyl, isobutyl, tert-butyl, n-pentyl or n-hexyl) or is linked to $R^4$ as defined above.

$R^9$ and $R^{10}$ each independently represent a hydrogen atom or a $C_1$–$C_6$, preferably $C_1$–$C_4$, alkyl group (e.g. methyl, ethyl, n-propyl, isopropyl, n-butyl, isobutyl, tert-butyl, n-pentyl or n-hexyl), or $R^9$ and $R^{10}$ together with the nitrogen atom to which they are attached form a 4- to 7-membered saturated heterocycle.

$R^1$1 and $R^{12}$ each independently represent a hydrogen atom or a $C_1$–$C_6$, preferably $C_1$–$C_4$, alkyl group (e.g. methyl, ethyl, n-propyl, isopropyl, n-butyl, isobutyl, tert-butyl, n-pentyl or n-hexyl) optionally substituted by a $C_1$–$C_6$, preferably $C_1$–$C_4$, alkoxycarbonyl substituent group.

$R^{13}$ represents a hydrogen atom or a $C_1$–$C_6$, preferably $C_1$–$C_4$, alkyl group (e.g. methyl, ethyl, n-propyl, isopropyl, n-butyl, isobutyl, tert-butyl, n-pentyl or n-hexyl).

$R^{14}$ represents a hydrogen atom, or a $C_1$–$C_6$, preferably $C_1$–$C_4$, alkyl group (e.g. methyl, ethyl, n-propyl, isopropyl, n-butyl, isobutyl, tert-butyl, n-pentyl or n-hexyl) optionally substituted by carboxyl, $C_1$–$C_6$, preferably $C_1$–$C_4$, alkoxy or $C_1$–$C_6$, preferably $C_1$–$C_4$, alkoxycarbonyl.

$R^{15}$ represents a group $C_2$–$C_6$, preferably $C_2$–$C_4$, alkyl group (e.g. ethyl, n-propyl, isopropyl, n-butyl, isobutyl, tert-butyl or n-pentyl), $C_2$–$C_6$, preferably $C_2$–$C_4$, alkenyl, $C_3$–$C_6$ cycloalkyl (e.g. cyclobutyl or cyclopentyl), $C_5$–$C_6$ cycloalkenyl, adamantyl, phenyl or a saturated or unsaturated 5- to 10-membered heterocyclic ring system comprising at least one heteroatom selected from nitrogen, oxygen and sulphur, wherein each group may be optionally substituted by one or more (e.g. one, two, three or four) substituents independently selected from nitro, hydroxyl, oxo, halogen (e.g.; fluorine, chlorine, bromine or iodine), carboxyl, $C_1$–$C_6$, preferably $C_1$–$C_4$, alkyl (e.g. methyl, ethyl, n-propyl, isopropyl, n-butyl, isobutyl, tert-butyl, n-pentyl or n-hexyl), $C_1$–$C_6$, preferably $C_1$–$C_4$, alkoxy (e.g. methoxy, ethoxy, n-propoxy or n-butoxy), $C_1$–$C_6$, preferably $C_1$–$C_4$, alkylthio (e.g. methylthio or ethylthio), $C_1$–$C_6$, preferably $C_1$–$C_4$, alkylcarbonyl (e.g. methylcarbonyl, ethylcarbonyl, n-propylcarbonyl, isopropylcarbonyl, n-butylcarbonyl, n-pentylcarbonyl or n-hexylcarbonyl), $C_1$–$C_6$, preferably $C_1$–$C_4$, alkoxycarbonyl (e.g. methoxycarbonyl or ethoxycarbonyl), phenyl and —NHC(O)—$R^{17}$.

The saturated or unsaturated 5- to 10-membered heterocyclic ring system may be monocyclic or polycyclic (e.g. bicyclic) and may comprise up to four heteroatoms independently selected from nitrogen, oxygen and sulphur. Examples of ring systems that may be used include pyrrolidinyl, piperidinyl, pyrazolyl, thiazolidinyl, thienyl, isoxazolyl, thiadiazolyl, pyrrolyl, furanyl, thiazolyl, indolyl, quinolinyl, benzimidazolyl, triazolyl, tetrazolyl and pyridinyl.

Each $R^{16}$ independently represents halogen (e.g. chlorine, fluorine, bromine or iodine), cyano, nitro, carboxyl, hydroxyl, $C_3$–$C_6$ cycloalkyl (cyclopropyl, cyclobutyl, cyclopentyl or cyclohexyl), $C_1$–$C_6$, preferably $C_1$–$C_4$, alkoxy (e.g. methoxy, ethoxy, n-propoxy or n-butoxy), $C_1$–$C_6$, preferably $C_1$–$C_4$, alkoxycarbonyl (e.g. methoxycarbonyl or ethoxycarbonyl), $C_1$–$C_6$, preferably $C_1$–$C_4$, haloalkyl (e.g. trifluoromethyl), $C_1$–$C_6$, preferably $C_1$–$C_4$, haloalkoxy (e.g. trifluoromethoxy), —$NR^{18}R^{19}$ $C_3$–$C_6$ cycloalkylamino (e.g. cyclopropylamino, cyclobutylamino, cyclopentylamino or cyclohexylamino), $C_1$–$C_6$, preferably $C_1$–$C_4$, alkylthio (e.g. methylthio or ethylthio), $C_1$–$C_6$, preferably $C_1$–$C_4$, alkylcarbonyl (e.g. methylcarbonyl, ethylcarbonyl, n-propylcarbonyl, isopropylcarbonyl, n-butylcarbonyl, n-pentylcarbonyl or n-hexylcarbonyl), $C_1$–$C_6$, preferably $C_1$–$C_4$, alkylcarbonylamino (e.g. methylcarbonylamino or ethylcarbonylamino), sulphonamido, $C_1$–$C_6$, preferably $C_1$–$C_4$, alkylsulphonyl (e.g. methylsulphonyl, ethylsulphonyl, n-propylsulphonyl, isopropylsulphonyl, n-butylsulphonyl, n-pentylsulphonyl or n-hexylsulphonyl), —$C(O)NR^{21}R^{22}$, —$NR^{23}C(O)$—$(NH)_yR^{24}$, phenyl, or $C_1$–$C_6$, preferably $C_1$–$C_4$, alkyl (e.g. methyl, ethyl, n-propyl, isopropyl, n-butyl, isobutyl, is tert-butyl, n-pentyl or n-hexyl) optionally substituted by carboxyl or $C_1$–$C_6$, preferably $C_1$–$C_4$, alkoxycarbonyl (e.g. methoxycarbonyl or ethoxycarbonyl).

Preferably, each $R^{16}$ independently represents halogen (particularly chlorine or fluorine), cyano, $C_1$–$C_4$ alkoxy (especially methoxy), $C_1$–$C_4$ alkoxycarbonyl (especially methoxycarbonyl), $C_1$–$C_4$ haloalkyl (especially trifluoromethyl), $C_1$–$C_4$ alkylcarbonyl (particularly methylcarbonyl), phenyl or $C_1$–$C_4$ alkyl (e.g. methyl or tert-butyl). Each $R^{16}$ is especially a halogen atom or methyl group.

$R^{17}$ represents a $C_1$–$C_6$, preferably $C_1$–$C_4$, alkyl group (e.g. methyl, ethyl, n-propyl, isopropyl, n-butyl, isobutyl, tert-butyl, n-pentyl or n-hexyl), amino or phenyl group.

$R^{18}$ and $R^{19}$ each independently represent a hydrogen atom or a $C_1$–$C_6$, preferably $C_1$–$C_4$, alkyl group (e.g. methyl, ethyl, n-propyl, isopropyl, n-butyl, isobutyl, tert-butyl, n-pentyl or n-hexyl), or $R^{19}$ and $R^{20}$ together with the nitrogen atom to which they are attached form a 4- to 7-membered saturated heterocycle.

$R^{20}$ and $R^{21}$ each independently represent a hydrogen atom or a $C_1$–$C_6$, preferably $C_1$–$C_4$, alkyl group (e.g. methyl, ethyl, n-propyl, isopropyl, n-butyl, isobutyl, tert-butyl, n-pentyl or n-hexyl) optionally substituted by a $C_1$–$C_6$, preferably $C_1$–$C_4$, alkoxycarbonyl substituent group.

$R^{22}$ represents a hydrogen atom or a $C_1$–$C_6$, preferably $C_1$–$C_4$, alkyl group (e.g. methyl, ethyl, n-propyl, isopropyl, n-butyl, isobutyl, tert-butyl, n-pentyl or n-hexyl).

$R^{23}$ represents a hydrogen atom, or a $C_1$–$C_6$, preferably $C_1$–$C_4$, alkyl group (e.g. methyl, ethyl, n-propyl, isopropyl, n-butyl, isobutyl, tert-butyl, n-pentyl or n-hexyl) optionally substituted by carboxyl, $C_1$–$C_6$, preferably $C_1$–$C_4$, alkoxy or $C_1$–$C_6$, preferably $C_1$–$C_4$, alkoxycarbonyl.

Preferred compounds of the invention include:

N-(5-Chloro-2-{3-[3-(4-chloro-phenoxy)-pyrrolidin-1-yl]-2-hydroxy-propoxy}-phenyl)-isobutyramide, Thiophene-2-carboxylic acid (2-{3-[3-(4-chloro-phenoxy)-pyrrolidin-1-yl]-2-hydroxy-propoxy}-phenyl)-amide, N-[(2-{3-[3-(4-Chloro-phenoxy)-pyrrolidin-1-yl]-2-hydroxy-propoxy}-phenylcarbamoyl)-methyl]-benzamide, Pyrazine-2-carboxylic acid (2-{3-[3-(4-chloro-phenoxy)-pyrrolidin-1-yl]-2-hydroxy-propoxy}-phenyl)-amide, Cyclohexanecarboxylic acid (2-{3-[3-(4-chloro-phenoxy)-pyrrolidin-1-yl]-2-hydroxy-propoxy}-phenyl)-amide, N-(2-{3-[3-(4-Chloro-phenoxy)-pyrrolidin-1-yl]-2-hydroxy-propoxy}-phenyl)-phthalamic acid methyl ester, N-(2-{3-[3-(4-Chloro-phenoxy)-pyrrolidin-1-yl]-2-hydroxy-propoxy}-phenyl)-3-hydroxy-butyramide, N-(2-{3-[3-(4-Chloro-phenoxy)-pyrrolidin-1-yl]-2-hydroxy-propoxy}-phenyl)-2-ureido-acetamide, 4-Acetylamino-N-(2-{3-[3-(4-chloro-phenoxy)-pyrrolidin-1-yl]-2-hydroxy-propoxy}-phenyl)-butyramide, 1-Acetyl-piperidine-4-carboxylic acid (2-{3-[3-(4-chloro-phenoxy)-pyrrolidin-1-yl]-2-hydroxy-propoxy}-phenyl)-amide, N-(2-{3-[3-(4-Chloro-phenoxy)-pyrrolidin-1-yl]-2-hydroxy-propoxy}-phenyl)-3-methoxy-benzamide, 2-Acetylamino-N-(2-{3-[3-(4-chloro-phenoxy)-pyrrolidin-1-yl]-2-hydroxy-propoxy}-phenyl)-3-methyl-butyramide, 2-Acetylamino-N-(2-{3-[3-(4-chloro-phenoxy)-pyrrolidin-1-yl]-2-hydroxy-propoxy}-phenyl)-3-hydroxy-butyramide, Adamantane-1-carboxylic acid (2-{3-[3-(4-chloro-phenoxy)-pyrrolidin-1-yl]-2-hydroxy-propoxy}-phenyl)-amide, 2-Acetylamino-N-(2-{3-[3-(4-chloro-phenoxy)-pyrrolidin-1-yl]-2-hydroxy-propoxy}-phenyl)-3-phenyl-propionamide, N-(2-{3-[3-(4-Chloro-phenoxy)-pyrrolidin-1-yl]-2-hydroxy-propoxy}-phenyl)-2-methoxy-benzamide, 5-Methyl-thiophene-2-carboxylic acid (2-{3-[3-(4-chloro-phenoxy)-pyrrolidin-1-yl]-2-hydroxy-propoxy}-phenyl)-amide, 1-Acetyl-pyrrolidine-2-carboxylic acid (2-{3-[3-(4-chloro-phenoxy)-pyrrolidin-1-yl]-2-hydroxy-propoxy}-phenyl)-amide, 1,5-Dimethyl-1H-pyrazole-3-carboxylic acid (2-{3-[3-(4-chloro-phenoxy)-pyrrolidin-1-yl]-2-hydroxy-propoxy}-phenyl)-amide, 5-Oxo-pyrrolidine-2-carboxylic acid (2-{3-[3-(4-chloro-phenoxy)-pyrrolidin-1-yl]-2-hydroxy-propoxy}-phenyl)-amide, 1H-Indole-6-carboxylic acid (2-{3-[3-(4-chloro-phenoxy)-pyrrolidin-1-yl]-2-hydroxy-propoxy}-phenyl)-amide, Cyclobutanecarboxylic acid (2-{3-[3-(4-chloro-phenoxy)-pyrrolidin-1-yl]-2-hydroxy-propoxy}-phenyl)-amide, N-(2-{3-[3-(4-Chloro-phenoxy)-pyrrolidin-1-yl]-2-hydroxy-propoxy}-phenyl)-propionamide, Pentanoic acid (2-{3-[3-(4-chloro-phenoxy)-pyrrolidin-1-yl]-2-hydroxy-propoxy}-phenyl)-amide, Pent-4-enoic acid (2-{3-[3-(4-chloro-phenoxy)-pyrrolidin-1-yl]-2-hydroxy-propoxy}-phenyl)-amide, Cyclopentanecarboxylic acid (2-{3-[3-(4-chloro-phenoxy)-pyrrolidin-1-yl]-2-hydroxy-propoxy}-phenyl)-amide, Cyclopropanecarboxylic acid (2-{3-[3-(4-chloro-phenoxy)-pyrrolidin-1-yl]-2-hydroxy-propoxy}-phenyl)-amide, N-(2-{3-[3-(4-Chloro-phenoxy)-pyrrolidin-1-yl]-2-hydroxy-propoxy}-phenyl)-isobutyramide, N-(2-{3-[3-(4-Chloro-phenoxy)-pyrrolidin-1-yl]-2-hydroxy-propoxy}-phenyl)-2-methylsulfanyl-acetamide, 2-Acetylamino-N-(2-{3-[3-(4-chloro-phenoxy)-pyrrolidin-1-yl]-2-hydroxy-propoxy}-phenyl)-propionamide, N-(2-{3-[3-(4-Chloro-phenoxy)-pyrrolidin-1-yl]-2-hydroxy-propoxy}-phenyl)-butyramide, N-(2-{3-[3-(4-Chloro-phenoxy)-pyrrolidin-1-yl]-2-hydroxy-propoxy}-phenyl)-3-methyl-butyramide, N-(2-{3-[3-(4-Chloro-phenoxy)-pyrrolidin-1-yl]-2-hydroxy-propoxy}-phenyl)-2-methoxy-acetamide, N-(2-{3-[3-(4-Chloro-phenoxy)-pyrrolidin-1-yl]-2-hydroxy-propoxy}-phenyl)-2,2-dimethyl-propionamide, 5-Oxo-hexanoic acid (2-{3-[3-(4-chloro-phenoxy)-pyrrolidin-1-yl]-2-hydroxy-propoxy}-phenyl)-amide, Hexanoic acid (2-{3-[3-(4-chloro-phenoxy)-pyrrolidin-1-yl]-2-hydroxy-propoxy}-phenyl)-amide, 2-Chloro-N-(2-{3-[3-(4-chloro-phenoxy)-pyrrolidin-1-yl]-2-hydroxy-propoxy}-phenyl)-benzamide, 3-Chloro-N-(2-{3-[3-(4-chloro-phenoxy)-pyrrolidin-1-yl]-2-hydroxy-propoxy}-phenyl)-benzamide, (4R)-N-(2-{3-[3-(4-chlorophenoxy)-1-pyrrolidinyl]-2-hydroxypropoxy}phenyl)-1,3-thiazolidine-4-carboxamide ditrifluoroacetate, Thiophene-2-carboxylic acid (2-{3-[4-(3,4-dichloro-phenoxy)-piperidin-1-yl]-2-hydroxy-propoxy}-phenyl)-amide, N-(2-{3-[4-(3,4-Dichloro-phenoxy)-piperidin-1-yl]-2-hydroxy-propoxy}-phenyl)-benzamide, N-(2-{3-[4-(3,4-Dichloro-phenoxy)-piperidin-1-yl]-2-hydroxy-propoxy}-phenyl)-nicotinamide, Pyridine-2-carboxylic acid (2-{3-[4-(3,4-dichloro-phenoxy)-piperidin-1-yl]-2-hydroxy-propoxy}-phenyl)-amide, N-(2-{3-[4-(3,4-Dichloro-phenoxy)-piperidin-1-yl]-2-hydroxy-propoxy}-phenyl)-isonicotinamide, Cyclohexanecarboxylic acid (2-{3-[4-(3,4-dichloro-phenoxy)-piperidin-1-yl]-2-hydroxy-propoxy}-phenyl)-amide, N-(2-{3-[4-(3,4-Dichloro-phenoxy)-piperidin-1-yl]-2-hydroxy-propoxy}-phenyl)-3-hydroxy-butyramide, 5-Methyl-thiophene-2-carboxylic acid (2-{3-[4-(3,4-dichloro-phenoxy)-piperidin-1-yl]-2-hydroxy-propoxy}-phenyl)-amide, Cyclobutanecarboxylic acid (2-{3-[4-(3,4-dichloro-phenoxy)-piperidin-1-yl]-2-hydroxy-propoxy}-phenyl)-amide, N-(2-{3-[4-(3,4-Dichloro-phenoxy)-piperidin-1-yl]-2-hydroxy-propoxy}-phenyl)-propionamide, Pentanoic acid (2-{3-[4-(3,4-dichloro-phenoxy)-piperidin-1-yl]-2-hydroxy-propoxy}-phenyl)-amide, Pent-4-enoic acid (2-{3-[4-(3,4-dichloro-phenoxy)-piperidin-1-yl]-2-hydroxy-propoxy}-phenyl)-amide, Cyclopentanecarboxylic acid (2-{3-[4-(3,4-dichloro-phenoxy)-piperidin-1-yl]-2-hydroxy-propoxy}-phenyl)-amide, N-(2-{3-[4-(3,4-Dichloro-phenoxy)-piperidin-1-yl]-2-hydroxy-propoxy}-phenyl)-3-methyl-butyramide, N-(2-{3-[3-(4-chlorophenoxy)-1-pyrrolidinyl]-2-hydroxypropoxy}phenyl)-2,2,2-trifluoroacetamide hydrochloride, 4-(2-{3-[4-(3,4-Dichloro-phenoxy)-piperidin-1-yl]-2-hydroxy-propoxy}-phenylcarbamoyl)-3-methyl-butyric acid, N-(2-{3-[4-(3,4-Dichloro-phenoxy)-piperidin-1-yl]-2-hydroxy-propoxy}-phenyl)-succinamic acid, Furan-2-carboxylic acid (2-{3-[3-(4-chloro-phenoxy)-pyrrolidin-1-yl]-2-hydroxy-propoxy}-4-methyl-phenyl)-amide, 1H-Pyrrole-2-carboxylic acid (2-{3-[3-(4-chloro-phenoxy)-pyrrolidin-1-yl]-2-hydroxy-propoxy}-4-methyl-phenyl)-amide, Thiophene-2-carboxylic acid (2-{3-[3-(4-chloro-phenoxy)-pyrrolidin-1-yl]-2-hydroxy-propoxy}-4-methyl-phenyl)-amide, Cyclopentanecarboxylic acid (2-{3-[3-(4-chloro-phenoxy)-pyrrolidin-1-yl]-2-hydroxy-propoxy}-4-methyl-phenyl)-amide, 5-Methyl-thiophene-2-carboxylic acid (2-{3-[3-(4-chloro-phenoxy)-pyrrolidin-1-yl]-2-hydroxy-propoxy}-4-methyl-phenyl)-amide, 3-Chloro-thiophene-2-carboxylic acid (2-{3-[3-(4-chloro-phenoxy)-pyrrolidin-1-yl]-2-hydroxy-propoxy}-4-methyl-phenyl)-amide, 5-Methyl-isoxazole-4-carboxylic acid (2-{3-[3-(4-chloro-phenoxy)-pyrrolidin-1-yl]-2-hydroxy-propoxy}-4-methyl-phenyl)-amide,

[1,2,3]Thiadiazole-4-carboxylic acid (2-{3-[3-(4-chloro-phenoxy)-pyrrolidin-1-yl]-2-hydroxy-propoxy}-4-methyl-phenyl)-amide, 3-Methyl-furan-2-carboxylic acid (2-{3-[3-(4-chloro-phenoxy)-pyrrolidin-1-yl]-2-hydroxy-propoxy}-4-methyl-phenyl)-amide, Cyclopent-1-enecarboxylic acid (2-{3-[3-(4-chloro-phenoxy)-pyrrolidin-1-yl]-2-hydroxy-propoxy}-4-methyl-phenyl)-amide, 2-Methyl-furan-3-carboxylic acid (2-{3-[3-(4-chloro-phenoxy)-pyrrolidin-1-yl]-2-hydroxy-propoxy}-4-methyl-phenyl)-amide, 3-Methyl-thiophene-2-carboxylic acid (2-{3-[3-(4-chloro-phenoxy)-pyrrolidin-1-yl]-2-hydroxy-propoxy}-4-methyl-phenyl)-amide, 5-Nitro-1H-pyrazole-3-carboxylic acid (2-{3-[3-(4-chloro-phenoxy)-pyrrolidin-1-yl]-2-hydroxy-propoxy}-4-methyl-phenyl)-amide, Thiophene-3-carboxylic acid (2-{3-[3-(4-chloro-phenoxy)-pyrrolidin-1-yl]-2-hydroxy-propoxy}-4-methyl-phenyl)-amide, Cyclobutanecarboxylic acid (2-{3-[3-(4-chloro-phenoxy)-pyrrolidin-1-yl]-2-hydroxy-propoxy}-4-methyl-phenyl)-amide, Furan-2-carboxylic acid (2-{3-[3-(4-fluoro-phenoxy)-pyrrolidin-1-yl]-2-hydroxy-propoxy}-4-methyl-phenyl)-amide, 1H-Pyrrole-2-carboxylic acid (2-{3-[3-(4-fluoro-phenoxy)-pyrrolidin-1-yl]-2-hydroxy-propoxy}-4-methyl-phenyl)-amide, Thiophene-2-carboxylic acid (2-{3-[3-(4-fluoro-phenoxy)-pyrrolidin-1-yl]-2-hydroxy-propoxy}-4-methyl-phenyl)-amide, 3-Chloro-thiophene-2-carboxylic acid (2-{3-[3-(4-fluoro-phenoxy)-pyrrolidin-1-yl]-2-hydroxy-propoxy}-4-methyl-phenyl)-amide, 5-Methyl-isoxazole-4-carboxylic acid (2-{3-[3-(4-fluoro-phenoxy)-pyrrolidin-1-yl]-2-hydroxy-propoxy}-4-methyl-phenyl)-amide, 3-Methyl-furan-2-carboxylic acid (2-{3-[3-(4-fluoro-phenoxy)-pyrrolidin-1-yl]-2-hydroxy-propoxy}-4-methyl-phenyl)-amide, Cyclopent-1-enecarboxylic acid (2-{3-[3-(4-fluoro-phenoxy)-pyrrolidin-1-yl]-2-hydroxy-propoxy}-4-methyl-phenyl)-amide, 2-Methyl-furan-3-carboxylic acid (2-{3-[3-(4-fluoro-phenoxy)-pyrrolidin-1-yl]-2-hydroxy-propoxy}-4-methyl-phenyl)-amide, 3-Methyl-thiophene-2-carboxylic acid (2-{3-[3-(4-fluoro-phenoxy)-pyrrolidin-1-yl]-2-hydroxy-propoxy}-4-methyl-phenyl)-amide, 5-Chloro-thiophene-2-carboxylic acid (2-{3-[3-(4-fluoro-phenoxy)-pyrrolidin-1-yl]-2-hydroxy-propoxy}-4-methyl-phenyl)-amide, Thiophene-3-carboxylic acid (2-{3-[3-(4-fluoro-phenoxy)-pyrrolidin-1-yl]-2-hydroxy-propoxy}-4-methyl-phenyl)-amide, 2,5-Dimethyl-furan-3-carboxylic acid (2-{3-[3-(4-fluoro-phenoxy)-pyrrolidin-1-yl]-2-hydroxy-propoxy}-4-methyl-phenyl)-amide, Cyclobutanecarboxylic acid (2-{3-[3-(4-fluoro-phenoxy)-pyrrolidin-1-yl]-2-hydroxy-propoxy}-4-methyl-phenyl)-amide, Furan-3-carboxylic acid (2-{3-[3-(4-fluoro-phenoxy)-pyrrolidin-1-yl]-2-hydroxy-propoxy}-4-methyl-phenyl)-amide, N-{2-[(3-{3-[(4-fluorophenyl)oxy]-1-pyrrolidinyl}-2-hydroxypropyl)oxy]-4-methylphenyl}-1H-pyrrole-2-carboxamide, N-{2-[(3-{3-[(4-chlorophenyl)oxy]-1-pyrrolidinyl}-2-hydroxypropyl)oxy]-4-methylphenyl}-3-thiophenecarboxamide, N-{2-[(3-{3-[(4-chlorophenyl)oxy]-1-pyrrolidinyl}-2-hydroxy-2-methylpropyl)oxy]phenyl}-2-thiophenecarboxamide, compound with trifluoroacetic acid, N-{2-[(3-{3-[(4-fluorophenyl)oxy]-1-pyrrolidinyl}-2-hydroxypropyl)oxy]-4-methylphenyl}-2-thiophenecarboxamide, N-{2-[(3-{3-[(4-chlorophenyl)oxy]-1-pyrrolidinyl}-2-hydroxypropyl)oxy]phenyl}-2-furancarboxamide, N-{2-[(3-{3-[(4-chlorophenyl)oxy]-1-pyrrolidinyl}-2-hydroxypropyl)oxy]phenyl}-1-pyrrole-2-carboxamide, N-{2-[(3-{3-[(4-chlorophenyl)oxy]-1-pyrrolidinyl}-2-hydroxypropyl)oxy]-4-methylphenyl}-1H-pyrrole-3-carboxamide, N-{2-[(3-{3-[(4-fluorophenyl)oxy]-1-pyrrolidinyl}-2-hydroxypropyl)oxy]-4-methylphenyl}-2-furancarboxamide, N-{2-[(3-{3-[(4-chlorophenyl)oxy]-1-pyrrolidinyl}-2-hydroxy-2-methylpropyl)oxy]phenyl}cyclopentanecarboxamide, compound with trifluoroacetic acid, N-(2-{3-[3-(4-Fluoro-phenoxy)-pyrrolidin-1--yl]-2-hydroxy-2-methyl-propoxy}-phenyl)-benzamide, N-(2-3{3-[3-(4-Cyano-phenoxy)-pyrrolidin-1-yl]-2-hydroxy-2-methyl-propoxy}-phenyl)-benzamide, N-(2-{3-[4-(3,4-Dichloro-phenoxy)-piperidin-1-yl]-2-hydroxy-2-methyl-propoxy}-phenyl)-benzamide, N-(2-{3-[3-(4-Chloro-phenoxy)-pyrrolidin-1-yl]-2-hydroxy-2-methyl-propoxy}-phenyl)-benzamide, and N-(2-{3-[4-(3,4-Dichloro-phenylamino)-piperidin-1-yl]-2-hydroxy-2-methyl-propoxy}-phenyl)-benzamide.

The present invention further provides a process for the preparation of a compound of formula (I) as defined above which comprises reacting a compound of general formula

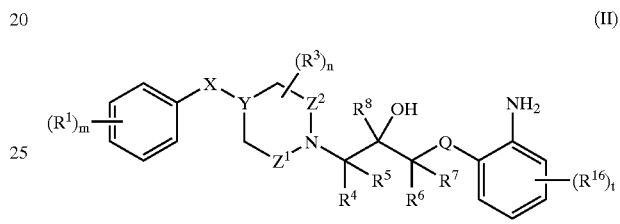

(II)

or a salt thereof (e.g. an acid addition salt such as a hydrochloride salt), wherein m, n, t, $R^1$, $R^3$, $R^4$, $R^5$, $R^6$, $R^7$, $R^8$, $R^{16}$, Q, $Z^1$ and $Z^2$ are as defined in formula (I), with a compound of general formula

$R^{15}$—$CO_2H$ (III)

or chemically equivalent derivative thereof (e.g. acyl halide or anhydride derivative) wherein $R^{15}$ is as defined in formula (I);

and optionally thereafter forming a pharmaceutically acceptable salt or solvate of the compound of formula (I) obtained.

The process of the invention may conveniently be carried out in a solvent, e.g. an organic solvent such as an alcohol (e.g. methanol or ethanol), a hydrocarbon (e.g. toluene), an amine (e.g. triethylamine or diisopropylethylamine) or acetonitrile at a temperature of, for example, 15° C. or above, such as a temperature in the range from 20 to 120° C.

Compounds of formulae (II) and (III) are either commercially available, are well known in the literature or may be prepared easily using known techniques.

It will be appreciated by those skilled in the art that in the process of the present invention certain functional groups such as hydroxyl or amino groups in the starting reagents or intermediate compounds may need to be protected by protecting groups. Thus, the preparation of the compounds of formula (I) may involve, at an appropriate stage, the removal of one or more protecting groups.

The protection and deprotection of functional groups is described in 'Protective Groups in Organic Chemistry', edited by J. W. F. McOmie, Plenum Press (1973) and 'Protective Groups in Organic Synthesis', 2nd edition, T. W. Greene and P. G. M. Wuts, Wiley-Interscience (1991).

The compounds of formula (I) above may be converted to a pharmaceutically acceptable salt or solvate thereof, preferably an acid addition salt such as a hydrochloride, hydrobromide, phosphate, acetate, fumarate, maleate, tartrate, citrate, oxalate, methanesulphonate or p-toluenesulphonate.

Compounds of formula (I) are capable of existing in stereoisomeric forms. It will be understood that the invention encompasses the use of all geometric and optical isomers of the compounds of formula (I) and mixtures thereof including racemates. The use of tautomers and mixtures thereof also form an aspect of the present invention.

The compounds of formula (I) have activity as pharmaceuticals, in particular as modulators of chemokine receptor (especially MIP-1α chemokine receptor) activity, and may be used in the treatment of autoinmnune, inflammatory, proliferative and hyperproliferative diseases and immunologically-mediated diseases including rejection of transplanted organs or tissues and Acquired Immunodeficiency Syndrome (AIDS).

Examples of these conditions are:
(1) (the respiratory tract) airways diseases including chronic obstructive pulmonary disease (COPD) such as irreversible COPD; asthma, such as bronchial, allergic, intrinsic, extrinsic and dust asthma, particularly chronic or inveterate asthma (e.g. late asthma and airways hyper-responsiveness); bronchitis; acute, allergic, atrophic rhinitis and chronic rhinitis including rhinitis caseosa, hypertrophic rhinitis, rhinitis purulenta, rhinitis sicca and rhinitis medicamentosa; membranous rhinitis including croupous, fibrinous and pseudomembranous rhinitis and scrofoulous rhinitis; seasonal rhinitis including rhinitis nervosa (hay fever) and vasomotor rhinitis; sarcoidosis, farmer's lung and related diseases, fibroid lung and idiopathic interstitial pneumonia;
(2) (bone and joints) rheumatoid arthritis, seronegative spondyloarthropathies (including ankylosing spondylitis, psoriatic arthritis and Reiter's disease), Behcet's disease, Sjogren's syndrome and systemic sclerosis;
(3) (skin) psoriasis, atopical dermatitis, contact dermatitis and other eczmatous dermitides, seborrhoetic dermatitis, Lichen planus, Pemphigus, bullous Pemphigus, Epidermolysis bullosa, urticaria, angiodermas, vasculitides, erythemas, cutaneous eosinophilias, uveitis, Alopecia areata and vernal conjunctivitis;
(4) (gastrointestinal tract) Coeliac disease, proctitis, eosinopilic gastro-enteritis, mastocytosis, Crohn's disease, ulcerative colitis, food-related allergies which have effects remote from the gut, e.g., migraine, rhinitis and eczema;
(5) (other tissues and systemic disease) multiple sclerosis, atherosclerosis, Acquired Immunodeficiency Syndrome (AIDS), lupus erythematosus, systemic lupus, erythematosus, Hashimoto's thyroiditis, myasthenia gravis, type I diabetes, nephrotic syndrome, eosinophilia fascitis, hyper IgE syndrome, lepromatous leprosy, sezary syndrome and idiopathic thrombocytopenia pupura;
(6) (allograft rejection) acute and chronic following, for example, transplantation of kidney, heart, liver, lung, bone marrow, skin and cornea; and chronic graft versus host disease;
(7) cancers, especially non-small cell lung cancer (NSCLC) and squamous sarcoma;
(8) diseases in which angiogenesis is associated with raised chemokine levels (e.g. NSCLC); and
(9) cystic fibrosis, stroke, re-perfusion injury in the heart, brain, peripheral limbs and sepsis.

Thus, the present invention provides a compound of formula (I), or a pharmaceutically-acceptable salt or solvate thereof, as hereinbefore defined for use in therapy.

In a further aspect, the present invention provides the use of a compound of formula (I), or a pharmaceutically acceptable salt or solvate thereof, as hereinbefore defined in the manufacture of a medicament for use in therapy.

In the context of the present specification, the term "therapy" also includes "prophylaxis" unless there are specific indications to the contrary. The terms "therapeutic" and "therapeutically" should be construed accordingly.

The invention also provides a method of treating an inflammatory disease in a patient suffering from, or at risk of, said disease, which comprises administering to the patient a therapeutically effective amount of a compound of formula (I), or a pharmaceutically acceptable salt or solvate thereof, as hereinbefore defined.

The invention still farther provides a method of treating an airways disease in a patient suffering from, or at risk of, said disease, which comprises administering to the patient a therapeutically effective amount of a compound of formula (I), or a pharmaceutically acceptable salt or solvate thereof, as hereinbefore defined.

For the above-mentioned therapeutic uses the dosage administered will, of course, vary with the compound employed, the mode of administration, the treatment desired and the disorder indicated. The daily dosage of the compound of formula (I) may be in the range from 0.001 mg/kg to 30 mg/kg.

The compounds of formula (I) and pharmaceutically acceptable salts and solvates thereof may be used on their own but will generally be administered in the form of a pharmaceutical composition in which the formula (I) compound/salt/solvate (active ingredient) is in association with a pharmaceutically acceptable adjuvant, diluent or carrier. Depending on the mode of administration, the pharmaceutical composition will preferably comprise from 0.05 to 99% w (per cent by weight), more preferably from 0.05 to 80% w, still more preferably from 0.10 to 70% w, and even more preferably from 0.10 to 50% w, of active ingredient, all percentages by weight being based on total composition.

The present invention also provides a pharmaceutical composition comprising a compound of formula (I), or a pharmaceutically acceptable salt or solvate thereof, as hereinbefore defined, in association with a pharmaceutically acceptable adjuvant, diluent or carrier.

The invention further provides a process for the preparation of a pharmaceutical composition of the invention which comprises mixing a compound of formula (I), or a pharmaceutically acceptable salt or solvate thereof, as hereinbefore defined, with a pharmaceutically acceptable adjuvant, diluent or carrier.

The pharmaceutical compositions may be administered topically (e.g. to the lung and/or airways or to the skin) in the form of solutions, suspensions, heptafluoroalkane aerosols and dry powder formulations; or systemically, e.g. by oral administration in the form of tablets, capsules, syrups, powders or granules, or by parenteral administration in the form of solutions or suspensions, or by subcutaneous administration or by rectal administration in the form of suppositories or transdermally.

The invention will now be further explained by reference to the following illustrative examples, in which $^1$H NMR spectra were recorded on Varian Unity Inova 400. The central solvent peak of chloroform-d ($\delta_H$ 7.27 ppm) were used as internal standard. Low resolution mass spectra and accurate mass determination were recorded on a Hewlett-Packard 100 LC-MS system equipped with APCI/ESI ionisation chambers. All solvents and commercial reagents were laboratory grade and used as received. The nomenclature used for the compounds was generated with ACD/IUPAC Name Pro. The following abbreviations are used in the examples:

NMP: 1-Methyl-2-pyrrolidinone
DIEA: N,N-Diisopropylethylamine
HBTU: 2-(1H-Benzotriazol-1-yl)-1,1,3,3-tetramethyluronium hexafluorophosphate
HoBT: 1-Hydroxybenzotriazole
THF: Tetrahydrofuran

EXAMPLE 1

N-(5-Chloro-{2-3-[3-(4-chloro-phenoxy)-pyrrolidin-1-yl]-2-hydroxy-propoxy}-phenyl)-isobutyramide
a) N-(5-Chloro-2-hydroxy-pheny)-isobutyramide In a flask was added 4-chloro-2-aminophenol (1.2 g, 8.39 mmole) and water (25 ml). The suspension was vigorously stirred and isobutyric anhydride (1.6 ml, 10.5 mmole) was added. The mixture was heated to 60° C. for 30 minutes under vigorous stirring. The emulsion was cooled, and a precipitate was formed, which was collected through filtration. The solid was washed twice with water on the filter and was finally dried to give 1.4 g (78%) of the sub-title compound as a white solid.

$^1$H-NMR(400 MHz, DMSO-d$_6$)δ: 10.11 (1H, s); 9.12 (1H, s); 7.94 (1H, d, J2.5 Hz); 6.95 (1H, dd, J 8.7 2.6 Hz); 6.84 (1H, d, J 8.5 Hz); 2.79 (1H, p, J 6.7 Hz); 1.08 (6H, d, J 6.8 Hz)

b) N-(5-Chloro-2-oxiranylmethoxy-phenyl)-isobutyramide

In a vial was added the compound obtained in a) (0.4 g, 1.87 mmole), epibromohydrin (0.28 g, 2.06 mmole), K$_2$CO$_3$ (0.5 g, 3.7 mmole) and DMF (2 ml). The vial was sealed and heated with stirring (2 hours, 60° C.). The mixture was then partitioned between EtOAc and water, and the organic phase was washed twice with water and once with brine, and was finally evaporated to give a brown solid. The crude epoxide was purified on silica, to give 0.22 g (44%) of the sub-title compound as a white solid.

c) In a vial was added the compound obtained in b) (0.026 g, 0.13 mmole), 3-(4-chlorophenoxy)-pyrrolidine (0.035 g, 0.13 mmole) in ethanol (2 ml). The vial was sealed and heated with stirring at 75° C. for 3 hours. The solution was allowed to cool, and the solvent was evaporated. The crude product was purified on silica, and the pure fractions were collected. The title compound was lyophilized as the hydrochloride, giving 0.055 g (84%) as a white solid. The compound was a mixture of four stereoisomers, which had an effect on the NMR-spectra.

$^1$H-NMR (400 MHz, DMSO-d$_6$)δ: 10.84–10.34 (1H, m); 9.12 (1H, s); 8.09 (1H, s); 7.36 (2H, dd, J 9.2 1.3 Hz); 7.11–7.00 (3H, m); 7.00 (2H, d, J 8.8 Hz); 6.22–6.06 (1H, m); 5.22–5.10 (1H, m); 4.34 (1H, bs); 4.08–3.96 (1.5H, m); 3.95–3.87 (1H, m); 3.83–3.66 (1.5H, m); 3.61–3.23 (3H, m); 2.86 (1H, sept, J 6.6 Hz); 2.64–2.51 (½H, m); 2.36–2.14 (1H, m); 2.14–2.00 (½H, m); 1.08 (6H, d, J 6.7 Hz)

APCI-MS: m/z 467.2 [MH+]

Aniline Intermediate 1
1-(2-aminophenoxy)-3-[4-(3,4-dichlorophenoxy)-1-piperidinyl]-2-propanol dihydrochloride N-(2-{3-[4-(3,4-dichlorophenoxy)-1-piperidinyl]-2-hydroxypropoxy}phenyl)acetamide (1.418 g, 3.13 mmol, prepared by analogy to Example 1) was dissolved in 50 ml HCl (35%/aq, puriss) and refluxed overnight. The product precipitated and was filtered and dried to give 0.835 g (65%) of the title compound.

APCI-MS m/z: 411, 413 [MH$^+$]

$^1$H NMR (400 MHz, CDCl$_3$): δ 8.39–3.31 (m, 2H), 7.3 1 (d, 1H), 7.01–6.98(m, 3H), 6.94–6.91(m, 1H), 6.75(dd, 1H), 4.31(m, 1H), 4.12–4.02 (m, 2H), 3.92(dd, 1H), 2.90(m, 1H), 2.69(m, 1H), 2.62–2.51(m, 2H), 2.46(dd, 1H), 2.34(m, 1H), 2.18(s, 3H), 2.04–1.93(m, 2H), 1.89–1.77(m, 2H).

Aniline Intermediate 2
1-[(2-aminophenyl)oxyl]-3-{3-[(4-chlorophenyl)oxyl-]1-pyrrolidinyl}-2-propanol dihydrochloride Prepared according to the method described in Aniline Intermediate 1.

APCI-MS m/z: 363, 365 [MH$^+$]

The intermediate anilines 1 and 2 described above were used in the following examples.

EXAMPLE 2

Thiophene-2-carboxylic acid (2-{3-[3-(4-chloro-phenoxy)-pyrrolidin-1-yl]-2-hydroxy-propoxy}-phenyl)-amide To a solution of 80 uL 0.2M 2-thiophenecarboxylic acid in NMP were HBTU (80 uL, 0.2M/NMP), HoBT (80 uL, 0.2M/NMP), DIEA (30 uL, 0.5M/NMP) and pyridine (30 uL, 0.5M/NMP) added and stirred for 30 minutes before 1-[(2-aminophenyl)oxy]-3-{3-[(4-chlorophenyl)oxy]-1-pyrrolidinyl}-2-propanol (75 uL, 0.2M/NMP) was added. The mixture was stirred overnight at room temperature before it was concentrated under reduced pressure to dryness. The product was diluted with 1000 uL dichloromethane and washed with with sat.NaHCO$_3$/aq (800 uL), 1.81% HCl/aq(800 uL) and sat. NaCl/aq. The organic layer was concentrated under reduced pressure to dryness and used without further purification. Yield 3.6mg, 51%

APCI-MS m/z: 473.2 [MH$^+$]

$^1$H NMR (400 MHz, CD$_3$OD): δ 8 7.88–7.85 (d, 1H), 7.74–7.65 (m, 2H), 7.34–7.28 (m, 2H), 7.27–7.21(m, 1H), 7.20–7.15 (m, 1H), 7.14–7.09 (dd, 1H), 7.06–7.00 (m, 1H), 6.96–6.91 (m, 2H), 5.18–5.12 (m, 1H), 4.39–4.30 (m, 1H), 4.19–3.24 (m, 9H), 2.66–2.11 (m, 3H)

The following Examples 3 to 53 were prepared by methods analogous to the method described in Example 2.

EXAMPLE 3

N-[(2-{3-[3-(4-Chloro-phenoxy)-pyrrolidin-1-yl]-2-hydroxy-propoxy}-phenylcarbamoyl)-methyl]-benzamide APCI-MS m/z: 524.3 [MH$^+$]

EXAMPLE 4

Pyrazine-2-carboxylic acid (2-{3-[3-(4-chloro-phenoxy)-pyrrolidin-1-yl]-2-hydroxy-propoxy}-phenyl)-amide APCI-MS m/z: 469.2 [MH$^+$]

EXAMPLE 5

Cyclohexanecarboxylic acid (2-{3-[3-(4-chloro-phenoxy)-pyrrolidin-1-yl]-2-hydroxy-propoxy}-phenyl)-amide APCI-MS m/z: 473.3 [MH$^+$]

EXAMPLE 6

N-(2-{3-[3-(4-Chloro-phenoxy)-pyrrolidin-1-yl]-2-hydroxy-propoxy}-phenyl)-phthalamic acid methyl ester APCI-MS m/z: 525.2 [MH$^+$]

EXAMPLE 7

N-(2-{3-[3-(4-Chloro-phenoxy)-pyrrolidin-1-yl]-2-hydroxy-propoxy}-phenyl)-3-hydroxy-butyramide APCI-MS m/z: 449.2 [MH$^+$]

EXAMPLE 8

N-(2-{3-[3-(4-Chloro-phenoxy)-pyrrolidin-1-yl]-2-hydroxy-propoxy}-phenyl-2-ureido-acetamide APCI-MS m/z: 463.2 [MH$^+$]

EXAMPLE 9
4-Acetylamino-N-(2-{3-[3-(4-chloro-phenoxy)-pyrrolidin-1-yl]-2-hydroxy-propoxy}-phenyl)-butyramide
APCI-MS m/z: 490.3 [MH$^+$]

EXAMPLE 10
1-Acetyl-piperidine-4-carboxylic acid (2-{3-[3-(4-chlorophenoxy)-pyrrolidin-1-yl]-2-hydroxy-propoxy}-phenyl)-amide
APCI-MS m/z: 516.3 [MH$^+$]

EXAMPLE 11
N-(2-{3-[3-(4-Chloro-phenoxy)-pyrrolidin-1-yl]-2-hydroxy-propoxy}-phenyl)-3-methoxy-benzamide
APCI-MS m/z: 497.2 [MH$^+$]

EXAMPLE 12
2-Acetylamino-N-(2-{3-[3-(4-chloro-phenoxy)-pyrrolidin-1-yl]-2-hydroxy-propoxy}-phenyl)-3-methyl-butyramide
APCI-MS m/z: 504.3 [MH$^+$]

EXAMPLE 13
2-Acetylamino-N-(2-{3-[3-(4-chloro-phenoxy)-pyrrolidin-1-yl]-2-hydroxy-propoxy}-phenyl)-3-hydroxy-butyramide
APCI-MS m/z: 506.2 [MH$^+$]

EXAMPLE 14
Adamantane-1-carboxylic acid (2-{3-[3-(4-chlorophenoxy)-pyrrolidin-1-yl]-2-hydroxy-propoxy}-phenyl)-amide
APCI-MS m/z: 525.3 [MH$^+$]

EXAMPLE 15
2-Acetylamino-N-(2-{3-[3-(4-chloro-phenoxy)-pyrrolidin-1-yl]-2-hydroxy-propoxy}-phenyl)-3-phenyl-propionamide
APCI-MS m/z: 552.3 [MH$^+$]

EXAMPLE 16
N-(2-{3-[3-(4-Chloro-phenoxy)-pyrrolidin-1-yl]-2-hydroxy-propoxy}-phenyl)-2-methoxy-benzamide
APCI-MS m/z: 497.2 [MH$^+$]

EXAMPLE 17
5-Methyl-thiophene-2-carboxylic acid (2-{3-[3-(4-chlorophenoxy)-pyrrolidin-1-yl]-2-hydroxy-propoxy}-phenyl)-amide
APCI-MS m/z: 487.2 [MH$^+$]

EXAMPLE 18
1-Acetyl-pyrrolidine-2-carboxylic acid (2-{3-[3-(4-chlorophenoxy)-pyrrolidin-1-yl]-2-hydroxy-propoxy}-phenyl)-amide
APCI-MS m/z: 502.3 [MH$^+$]

EXAMPLE 19
1,5-Dimethyl-1H-pyrazole-3-carboxylic acid (2-{3-[3-(4-chloro-phenoxy)-pyrrolidin-1-yl]-2-hydroxy-propoxy}-phenyl)-amide
APCI-MS m/z: 485.3 [MH$^+$]

EXAMPLE 20
5-Oxo-pyrrolidine-2-carboxylic acid (2-{3-[3-(4-chlorophenoxy)-pyrrolidin-1-yl]-2-hydroxy-propoxy}-phenyl)-amide
APCI-MS m/z: 474.2 [MH$^+$]

EXAMPLE 21
1H-Indole-6-carboxylic acid (2-{3-[3-($^4$-chloro-phenoxy)-pyrrolidin-1-yl1-2-hydroxy-propoxy}-phenyl)-amide
APCI-MS m/z: 506.2 [MH$^+$]

EXAMPLE 22
Cyclobutanecarboxylic acid (2-{3-[3-(4-chloro-phenoxy)-pyrrolidin-1-yl]-2-hydroxy-propoxy}-phenyl)-amide
APCI-MS m/z: 445.3 [MH$^+$]

EXAMPLE 23
N-(2-{3-[3-(4-Chloro-phenoxy)-pyrrolidin-1-yl]-2-hydroxy-propoxy}-phenyl) propionamide
APCI-MS m/z: 419.2 [MH$^+$]

EXAMPLE 24
Pentanoic acid (2-{3-[3-(4-chloro-phenoxy)-pyrrolidin-1-yl]-2-hydroxy-propoxy}-phenyl)-amide
APCI-MS m/z: 447.3 [MH$^+$]

EXAMPLE 25
Pent-4-enoic acid (2-{3-[3-(4-chloro-phenoxy)-pyrrolidin-1-yl]-2-hydroxy-propoxy}-phenyl)-amide
APCI-MS m/z: 445.3 [MH$^+$]

EXAMPLE 26
Cyclopentanecarboxylic acid (2-{3-[3-(4-chloro-phenoxy)-pyrrolidin-1-yl]-2-hydroxy-propoxy}-phenyl)-amide
APCI-MS m/z: 459.3 [MH$^+$]

EXAMPLE 27
Cyclopropanecarboxylic acid (2-{3-[3-(4-chloro-phenoxy)-pyrrolidin-1-yl]-2-hydroxy-propoxy}-phenyl)-amide
APCI-MS m/z: 431.2 [MH$^+$]

EXAMPLE 28
N-(2-{3-[3-(4-Chloro-phenoxy)-pyrrolidin-1-yl]-2-hydroxy-propoxy}-phenyl)-isobutyramide APCI-MS m/z: 433.3 [MH$^+$]

EXAMPLE 29
N-(2-{3-[3-(4-Chloro-phenoxy)-pyrrolidin-1-yl]-2-hydroxy-propoxy}-phenyl)-2-methylsulfanyl-acetamide
APCI-MS m/z: 451.2 [MH$^+$]

EXAMPLE 30
2-Acetylamino-N-(2-{3-[3-(4-chloro-phenoxy)-pyrrolidin-1-yl]-2-hydroxy-propoxy}-phenyl)-propionamide
APCI-MS m/z: 476.2 [MH$^+$]

EXAMPLE 31
N-(2-{3-[3-(4-Chloro-phenoxy)-pyrrolidin-1-yl]-2-hydroxy-propoxy}-phenyl)-butyramide
APCI-MS m/z: 433.3 [MH$^+$]

EXAMPLE 32
N-(2-{3-[3-(4-Chloro-phenoxy)-pyrrolidin-1-yl]-2-hydroxy-propoxy}-phenyl)-3-methyl-butyramide
APCI-MS m/z: 447.3 [MH$^+$]

EXAMPLE 33
N-(2-{3-[3-(4-Chloro-phenoxy)-pyrrolidin-1-yl]-2-hydroxy-propoxy}-phenyl)-2-methoxy-acetamide
APCI-MS m/z: 435.2 [MR$^+$]

EXAMPLE 34
N-(2-{3-[3-(4-Chloro-phenoxy)-pyrrolidin-1-yl]-2-hydroxy-propoxyl-phenyl})-2,2-dimethyl-propionamide
APCI-MS m/z: 447.2 [MH$^+$]

EXAMPLE 35
5-Oxo-hexanoic acid (2-{3-[3-(4-chloro-phenoxy)-pyrrolidin-1-yl]-2-hydroxy-propoxy}-phenyl)-amide
APCI-MS m/z: 475.3 [MH$^+$]

EXAMPLE 36
Hexanoic acid (2-{3-[3-(4-chloro-phenoxy)-pyrrolidin-1-yl]-2-hydroxy-propoxy}-phenyl)-amide
APCI-MS m/z: 461.3 [MH$^+$]

EXAMPLE 37
2-Chloro-N-(2-{3-[3-(4-chloro-phenoxy)-pyrrolidin-1-yl]-2-hydroxy-propoxy}-phenyl)-benzamide
APCI-MS m/z: 501.2, 503.2 [MH$^+$]

EXAMPLE 38
3-Chloro-N-(2-{3-[3-(4-chloro-phenoxy)-pyrrolidin-1-yl]-2-hydroxy-propoxy}-phenyl)-benzamide
APCI-MS m/z: 501.2, 503.2 [MH$^+$]

EXAMPLE 39
(4R)-N-(2-{3-[3-(4-chlorophenoxy)-1-pyrrolidinyl]-2-hydroxypropoxy}phenyl)-1.3-thiazolidine-4-carboxamide ditrifluoroacetate
APCI-MS m/z: 478.2 [MH$^+$]

EXAMPLE 40
Thiophene-2-carboxylic acid (2-{3-[4-(3,4-dichloro-phenoxy)-piperidin-1-yl]-2-hydroxy-propoxy}-phenyl)-amide
APCI-MS m/z: 521.0, 523.0 [MH$^+$]

EXAMPLE 41
N-(2-{3-[4-(3,4-Dichloro-phenoxy)-piperidin-1-yl]-2-hydroxy-propoxy}-phenyl)-benzamide
APCI-MS m/z: 515.2, 517.2[MH$^+$]

EXAMPLE 42
N-(2-{3-[4-(3,4-Dichloro-phenoxy)-piperidin-1-yl]-2-hydroxy-propoxy}-phenyl)-nicotinamide
APCI-MS m/z: 516.2, 518.2 [MH$^+$]

EXAMPLE 43
Pyridine-2-carboxylic acid (2-{3-[4-(3,4-dichloro-phenoxy)-piperidin-1-yl]-2-hydroxy-propoxy}-phenyl)-amide
APCI-MS m/z: 516.2, 518.2 [MH$^+$]

EXAMPLE 44
N-(2-{3-[4-(3,4-Dichloro-phenoxy)-piperidin-1-yl]-2-hydroxy-propoxy}-phenyl)-isonicotinamide
APCI-MS m/z: 516.2, 518.2 [MH$^+$]

EXAMPLE 45
Cyclohexanecarboxylic acid (2-{3-[4-(3,4-dichloro-phenoxy)-piperidin-1-yl]-2-hydroxy-propoxy}-phenyl)-amide
APCI-MS m/z: 521.3, 523.3 [MH$^+$]

EXAMPLE 46
N-(2-{3-[4-(3,4-Dichloro-phenoxy)-piperidin-1-yl]-2-hydroxy-propoxy}-phenyl)-3-hydroxy-butyramide
APCI-MS m/z: 497.2, 499.3 [MH$^+$]

EXAMPLE 47
5-Methyl-thiophene-2-carboxylic acid (2-{3-[4-(3,4-dichloro-phenoxy)-piperidin-1-yl]-2-hydroxy-propoxy}-phenyl)-amide
APCI-MS m/z: 535.2, 537.2 [MH$^+$]

EXAMPLE 48
Cyclobutanecarboxylic acid (2-{3-[4-(3,4-dichloro-phenoxy)-piperidin-1-yl]-2-hydroxy-propoxy}-phenyl)-amide
APCI-MS m/z:493.3, 495.2 [MH$^+$]

EXAMPLE 49
N-(2-(3-[4-(3,4-Dichloro-phenoxy)-piperidin-1-yl]-2-hydroxy-propoxyl-phenyl)-propionamide
APCI-MS m/z: 467.2, 469.2 [MH$^+$]

EXAMPLE 50
Pentanoic acid (2-{3-[4-(3,4-dichloro-phenoxy)-piperidin-1-yl]-2-hydroxy-propoxy}-phenyl)-amide
APCI-MS m/z: 495.3, 497.3 [MH$^+$]

EXAMPLE 51
Pent-4-enoic acid (2-{3-14-(3,4-dichloro-phenoxy)-piperidin-1-yl]-2-hydroxy-propoxy}-phenyl)-amide
APCI-MS m/z: 493.3 ,495.2 [MH$^+$]

EXAMPLE 52
Cyclopentanecarboxylic acid (2-{3-[4-(3,4-dichloro-phenoxy)-piperidin-1-yl]-2-hydroxy-propoxy}-phenyl)-amide
APCI-MS m/z: 507.3, 509.3 [MH$^+$]

EXAMPLE 53
N-(2-13-[4-(3,4-Dichloro-phenoxy)-piperidin-1-yl]-2-hydroxy-propoxyl-phenyl)-3-methyl-butyramide
APCI-MS m/z: 495.3,497.3 [MH$^+$]

EXAMPLE 54
N-(2-{3-[3-(4-chlorophenoxy)-1-pyrrolidinyl]-2-hydroxypropoxy}phenyl)-2,2,2-trifluoroacetamide hydrochloride A mixture of 1-(2-aminophenoxy)-3-[3-(4-chlorophenoxy)-1-pyrrolidinyl]-2-propanol (10 mg, 0.022 mmol), dichloromethane (3 ml) and Triethyl amine was cooled in an ice bath. A solution of Trifluoro acetic anhydride (3.51 µl, 0.025 mmol) in dichloromethane (2 ml) was then added and the mixture stirred at 0° C. until reaction completion. The mixture was diluted with dichloromethane, washed with 1M H$_2$SO$_4$, water, dried over natrium sulphate and concentrated to give an oil. The oil was treated with 1.0M ethereal HCl solution to give the product as solid (9 mg).
APCI-MS: m/z 459, 460 [MH$^+$]

EXAMPLE 55
4-(2-{3-[4-(3,4-Dichloro-phenoxy)-piperidin-1-yl]-2-hydroxy-propoxy}-phenylcarbamoyl)-3-methyl-butyric acid 1-(2-aminophenoxy)-3-[4-(3,4-dichlorophenoxy)-1-piperidinyl]-2-propanol (75 uL, 0.2M/NMP) was mixed with 3-methyl glutaric anhydride (3 eq, 225 uL 0.2M /NMP) to get a product containing both ester and amide. After evaporation of the mixture it was treated with 3 eq 0.5M LiOH in (THF/water 1:4) for two hours at 80° C. to hydrolyse the ester. The reaction mixture was diluted with more water (2 mL) and the desired product was extracted with 5×500 uL EtOAc which was evaporated to dryness.
APCI-MS m/z: 539.2, 541.2 [MH$^+$]

EXAMPLE 56
N-(2-{3-[4-(3,4-Dichloro-phenoxy)-piperidin-1-yl]-2-hydroxy-propoxy}-phenyl)-succinamic acid
Prepared according to the method described in Example 55.
APCI-MS m/z: 511.2, 513.2 [MH$^+$]

Aniline Intermediate 3
1-(2-amino-5-methylphenoxy)-3-[3-(4-chlorophenoxy)-1-pyrrolidinyl]-2-propanol
APCI-MS m/z: 377.2, 379.1 [MH$^+$]
$^1$H NMR (400MHz, CDCl3): δ 7.26–7.21 (m, 2H), 6.79–6.74 (m, 2H), 6.67–6.62 (m, 3H), 4.83–4.76 (m, 1H), 4.15–4.06 (m, 1H), 4.04–4.00 (d, 2H), 3.73–3.64 (s, 2H), 3.47–3.35 (s, 1H), 3.14 –2.56 (m, 6H), 2.36–2.22(m, 4H), 2.05–1.95(m, 1H)

Aniline Intermediate 4
1-(2-amino-5-methylphenoxy)-3-[3-(4-fluorophenoxy)-1-pyrrolidinyl]-2-propanol
APCI-MS mz: 361.1 [MH$^+$]
$^1$H NMR (400MHz, CDCl3): δ 7.00–6.94 (m, 2H), 6.81–6.76 (m, 2H), 6.67–6.62 (m, 3H), 4.81–4.74 (m, 1H), 4.15–4.06 (m, 1H), 4.03–3.99 (m, 2H), 3.88–3.36 (m, 3H), 3.12–2.56 (m, 6H), 2.33–2.23(m, 4H), 2.05–1.96(m, 1H)

The compounds of Examples 57 to 85 were prepared using one of the Aniline Intermediates 3 and 4.

EXAMPLE 57
Furan-2-carboxylic acid (2-{3-[3-(4-chloro-phenoxy)-pyrrolidin-1-yl]-2-hydroxy-propoxy}4-methyl-phenyl)-amide
APCI-MS m/z: 471.5, 473.5 [MH$^+$]

EXAMPLE 58
1H-Pyrrole-2-carboxylic acid (2-{3-[3-(4-chloro-phenoxy)-pyrrolidin-1-yl]-2-hydroxy-propoxy}-4-methyl-phenyl)-amide
APCI-MS m/z: 470.5, 472.5 [MH$^+$]

EXAMPLE 59
Thiophene-2-carboxylic acid (2-{3-[3-(4-chloro-phenoxy)-pyrrolidin-1-yl]-2-hydroxy-propoxy}-4-methyl-phenyl)-amide
APCI-MS m/z: 487.5, 489.5 [MH$^+$]

EXAMPLE 60
Cyclopentanecarboxylic acid (2-{3-[3-(4-chloro-phenoxy)-pyrrolidin-1-yl]-2-hydroxy-propoxy}-4-methyl-phenyl)-amide
APCI-MS m/z: 473.6, 475.5 [MH$^+$]

EXAMPLE 61
5-Methyl-thiophene-2-carboxylic acid (2-{3-[3-(4-chloro-phenoxy)-pyrrolidin-1-yl]-2-hydroxy-propoxy}-4-methyl-phenyl)-amide
APCI-MS m/z: 501.5, 503.5 [MH$^+$]

EXAMPLE 62
3-Chloro-thiophene-2-carboxylic acid (2-{3-[3-(4-chloro-phenoxy)-pyrrolidin-1-yl]-2-hydroxy-propoxy}-4-methyl-phenyl)-amide
APCI-MS m/z: 521.5, 532.5 [MH$^+$]

EXAMPLE 63
5-Methyl-isoxazole-4-carboxylic acid (2-{3-[13-(4-chloro-phenoxy)-pyrrolidin-1-yl]-2-hydroxy-propoxy}-4-methyl-phenyl)-amide
APCI-MS m/z: 486.5, 488.6 [MH$^+$]

EXAMPLE 64
[1,2,3]Thiadiazole4-carboxylic acid (2-{3-[3-(4-chloro-phenoxy)-pyrrolidin-1-yl]-2-hydroxy-propoxy}-4-methyl-phenyl)-amide
APCI-MS m/z: 489.5, 491.5[MH$^+$]

EXAMPLE 65
3-Methyl-furan-2-carboxylic acid (2-{3-[3-(4-chloro-phenoxy)-pyrrolidin-1-yl]-2-hydroxy-propoxy}-4-methyl-phenyl)-amide
APCI-MS m/z: 485.5, 487.6 [MH$^+$]

EXAMPLE 66
Cyclopent-1-enecarboxylic acid (2-{3-[3-(4-chloro-phenoxy)-pyrrolidin-1-yl]-2-hydroxy-propoxy}-4-methyl-phenyl)-amide
APCI-MS m/z: 471.6, 473.6 [MH$^+$]

EXAMPLE 67
2-Methyl-furan-3-carboxylic acid (2-{3-[3-(4-chloro-phenoxy)-pyrrolidin-1-yl]-2-hydroxy-propoxy}-4-methyl-phenyl)-amide
APCI-MS m/z: 485.6, 487.6 [MH$^+$]

EXAMPLE 68
3-Methyl-thiophene-2-carboxylic acid (2-{3-[3-(4-chloro-phenoxy)-pyrrolidin-1-yl]-2-hydroxy-propoxy}-4-methyl-phenyl)-amide
APCI-MS m/z: 501.6, 503.5 [MH$^+$]

EXAMPLE 69
5-Nitro-1H-pyrazole-3-carboxylic acid (2-{3-[3-(4-chloro-phenoxy)-pyrrolidin-1-yl]-2-hydroxy-propoxy}-4-methyl-phenyl)-amide
APCI-MS m/z: 516.5, 518.5 [MH+]

EXAMPLE 70
Thiophene-3-carboxylic acid (2-{3-[3-(4-chloro-phenoxy)-pyrrolidin-1-yl]-2-hydroxy-propoxy}-4-methyl-phenyl)-amide
APCI-MS m/z: 487.5, 489.5 [MH+]

EXAMPLE 71
Cyclobutanecarboxylic acid (2-{3-[3-(4-chloro-phenoxy)-pyrrolidin-1-yl]-2-hydroxy-propoxy}-4-methyl-phenyl)-amide
APCI-MS m/z: 459.5,461.5 [MH+]

EXAMPLE 72
Furan-2-carboxylic acid (2-{3-[3-(4-fluoro-phenoxy)-pyrrolidin-1-yl]-2-hydroxy-propoxy}-4-methyl-phenyl)-amide
APCI-MS m/z: 455.5 [MH+]

EXAMPLE 73
1H-Pyrrole-2-carboxylic acid (2-{3-[3-(4-fluoro-phenoxy)-pyrrolidin-1-yl]-2-hydroxy-propoxy}-4-methyl-phenyl)-amide
APCI-MS m/z: 454.6 [MH+]

EXAMPLE 74
Thiophene-2-carboxylic acid (2-{3-[3-(4-fluoro-phenoxy)-pyrrolidin-1-yl]-2-hydroxy-propoxy}-4-methyl-phenyl)-amide
APCI-MS m/z: 471.5 [MH+]

EXAMPLE 75
3-Chloro-thiophene-2-carboxylic acid (2-{3-[3-(4-fluoro-phenoxy)-pyrrolidin-1-yl]-2-hydroxy-propoxy}-4-methyl-phenyl)-amide
APCI-MS m/z: 505.5, 507.5 [MH+]

EXAMPLE 76
5-Methyl-isoxazole-4-carboxylic acid (2-{3-[3-(4-fluoro-phenoxy)-pyrrolidin-1-yl]-2-hydroxy-propoxy}-4-methyl-phenyl)-amide
APCI-MS m/z: 470.5 [MH+]

EXAMPLE 77
3-Methyl-furan-2-carboxylic acid (2-{3-[3-(4-fluoro-phenoxy)-pyrrolidin-1-yl]-2-hydroxy-propoxy}-4-methyl-phenyl)-amide
APCI-MS m/z: 469.6 [MH+]

EXAMPLE 78
Cyclopent-1-enecarboxylic acid (2-{3-[3-(4-fluoro-phenoxy)-pyrrolidin-1-yl]-2-hydroxy-propoxy}-4-methyl-phenyl)-amide
APCI-MS m/z: 455.6 [MH+]

EXAMPLE 79
2-Methyl-furan-3-carboxylic acid (2-{3-[3-(4-fluoro-phenoxy)-pyrrolidin-1-yl]-2-hydroxy-propoxy}-4-methyl-phenyl)-amide
APCI-MS m/z: 469.6 [MH+]

EXAMPLE 80
3-Methyl-thiophene-2-carboxylic acid (2-{3-[3-(4-fluoro-phenoxy)-pyrrolidin-1-yl]-2-hydroxy-propoxy}-4-methyl-phenyl)-amide
APCI-MS m/z: 485.5 [MH+]

EXAMPLE 81
5-Chloro-thiophene-2-carboxylic acid (2-{3-[3-(4-fluoro-phenoxy)-pyrrolidin-1-yl]-2-hydroxy-propoxy}-4-methyl-phenyl)-amide
APCI-MS m/z: 505.5, 507.5 [MH+]

EXAMPLE 82
Thiophene-3-carboxylic acid (2-{3-[3-(4-fluoro-phenoxy)-pyrrolidin-1-yl]-2-hydroxy-propoxy}4-methyl-phenyl)-amide
APCI-MS m/z: 471.5 [MH+]

EXAMPLE 83
2,5-Dimethyl-furan-3-carboxylic acid (2-{3-[3-(4-fluoro-phenoxy)-pyrrolidin-1-yl]-2-hydroxy-propoxy}-4-methyl-phenyl)-amide
APCI-MS m/z: 483.6 [MH+]

EXAMPLE 84
Cyclobutanecarboxylic acid (2-{3-[3-(4-fluoro-phenoxy)-pyrrolidin-1-yl]-2-hydroxy-propoxy}-4-methyl-phenyl)-amide
APCI-MS m/z: 443.6 [MH+]

EXAMPLE 85
Furan-3-carboxylic acid (2-{3-[3-(4-fluoro-phenoxy)-pyrrolidin-1-yl]-2-hydroxy-propoxy}-4-methyl-phenyl)-amide
APCI-MS m/z: 455.5 [MH+]

EXAMPLE 86
N-{2-[(3-{3-[(4-fluorophenyl)oxy]-1-pyrrolidinyl}-2-hydroxypropyl)oxy]-4-methylphenyl}-1H-pyrrole-2-carboxamide
APCI-MS: m/z 454.1 [MH$^+$]

EXAMPLE 87
N-{2-[(3-{3-[(4-chlorophenyl)oxy]-1-pyrrolidinyl}-2-hydroxypropyl)oxy]-4-methylphenyl}-3-thiophenecarboxamide
APCI-MS: m/z 471.1 [MH$^+$]

EXAMPLE 88
N-{2-[(3-{3-[(4-chlorophenyl)oxy]-1-pyrrolidinyl}-2-hydroxy-2-methylpropyl)oxy]phenyl}-2-thiophenecarboxamide, compound with trifluoroacetic acid Aniline intermediate 3 (60 mg, 0.159 mmol), 2-thiophenecarboxylic acid (20.4 mg, 0.159 mmol) and HATU (72 mg, 0.191 mmol) were stirred in dichloromethane (2 ml).

Diisopropylethylamine was added to pH 8. The mixture was stirred overnight and then concentrated. The residue was purified on silica (dichloromethane/methanol 98/2) followed by purification on C18 (2 g Isolute, acetonitrile/water 20/80 to 35/65 with 0.5% trifluoroacetic acid) to give the title compound (75 mg, 79%).

$^1$H-NMR (400MHz, MeOD): δ 7.86 (m, 1H), 7.72 (m, 1H), 7.50 (m, 1H), 7.29 (m, 3H), 7.16 (m, 2H), 7.07 (m, 1H), 6.91 (m, 2H), 5.10 (m, 1H), 3.82–4.17 (m, 4H), 3.24–3.69 (m, 4H), 2.13–2.64 (m, 2H), 1.38 (m, 3H).

MS-APCI+: m/z 487 [MH$^+$]

EXAMPLE 89
N-{2-[(3-{3-[(4-fluorophenyl)oxy]-1-pyrrolidinyl}-2-hydroxypropyl)oxy]-4-methylphenyl}-2-thiophenecarboxamide
APCI MS APCI-MS: m/z 471.1 [MH$^+$]

EXAMPLE 90
N-{2-[(3-{3-[(4-chlorophenyl)oxy]-1-pyrrolidinyl}-2-hydroxypropyl)oxy]phenyl}-2-furancarboxamide
APCI-MS: m/z 456.9 [MH$^+$]

EXAMPLE 91
N-{2-[(3-{3-[(4-chlorophenyl)oxy]-1-pyrrolidinyl}-2-hydroxypropyl)oxylphenyl}-1-pyrrole-2-carboxamide
APCI-MS: m/z 456.1 [MH$^+$]

EXAMPLE 92
N-{2-[(3-{3-[(4-chlorophenyl)oxy]-1-pyrrolidinyl}-2hydroxypropyl)oxy]4-methylphenyl}-1H-pyrrole-3-carboxamide
APCI-MS: m/z 470.0 [MH$^+$]

EXAMPLE 93
N-{2-[(3-{3-[(4-fluorophenyl)oxy]-1-pyrrolidinyl}-2-hydroxypropyl)oxy]-4-methylphenyl}-2-furancarboxamide
APCI-MS: m/z 455.1 [MH$^+$]

EXAMPLE 94

N-{2-[(3-{3-[(4-chlorophenyl)oxy]-1-pyrrolidinyl}-2-hydroxy-2-methylpropyl)oxy]phenyl}cyclopentanecarboxamide, compound with trifluoracetic acid The compound (80 mg, 86%) was prepared from aniline intermediate 3 (60 mg, 0.159 mmol) and cyclopentanecarboxylic acid (18 µl, 0.159 mmol) as described in Example 88.

$^1$H-NMR (400MHz, MeOD): δ 7.59 (m, 1H), 7.29 (m, 2H), 7.19 (m, 1H), 7.09 (m, 1H), 6.97 (m, 3H), 5.17 (m, 1H), 3.86–4.23 (m, 4H), 3.35–3.73 (m, 4H), 2.86 (m, 1H), 1.45 (bs, 3H).

MS-APCI+: m/z 473 [MH$^+$]

EXAMPLE 95

N-(2-{3-[3-(4-Fluoro-phenoxy)-pyrrolidin-1-yl]-2-hydroxy-2-methyl-propoxy}-phenyl)-benzamide The compound was prepared using an analogous method as in Example 88.

APCI-MS: m/z 465 [MH$^+$]

EXAMPLE 96

N-(2-{3-[3-(4-Cyano-phenoxy)-pyrrolidin-1-yl]-2-hydroxy-2-methyl-propoxy}-phenyl)-benzamide The compound was prepared using an analogous method as in Example 88.

APCI-MS: m/z 472 [MH$^+$]

EXAMPLE 97

N-(2-{3-[4-(3,4-Dichloro-phenoxy)-piperidin-1-yl]-2-hydroxy-2-methyl-propoxy}-phenyl)-benzamide The compound was prepared using an analogous method as in Example 88.

APCI-MS: m/z 529 [MH$^+$]

EXAMPLE 98

N-(2-{3-[3-(4-Chloro-phenoxy)-pyrrolidin-1-yl]-2-hydroxy-2-methyl-propoxy}-phenyl)-benzamide The compound was prepared using an analogous method as in Example 88.

APCI-MS: m/z 481 [MH$^+$]

EXAMPLE 99

N-(2-{3-[4-(3,4-Dichloro-phenylamino)-piperidin-1-yl]-2-hydroxy-2-methyl-propoxy}-phenyl)-benzamide The compound was prepared using an analogous method as in Example 88.

APCI-MS: m/z 528 [MH$^+$]

THP-1 Chemotaxis Assay

Introduction

The assay measured the chemotactic response elicited by MIP-1α chemokine in the human monocytic cell line THP-1. The compounds of the Examples were evaluated by their ability to depress the chemotactic response to a standard concentration of MIP-1 α chemokine.

Methods

Culture of THP-1 cells

Cells were thawed rapidly at 37° C. from frozen aliquots and resuspended in a 25 cm flask containing 5 ml of RPMI-1640 medium supplemented with Glutamax and 10% heat inactivated fetal calf serum without antibiotics (RPMI+10% HIFCS). At day 3 the medium is discarded and replaced with fresh medium.

THP-1 cells are routinely cultured in RPMI-1640 medium supplemented with 10% heat inactivated fetal calf serum and glutamax but without antibiotics. Optimal growth of the cells requires that they are passaged every 3 days and that the minimum subculture density is 4×10+5 cells/ml.

Chemotaxis assay

Cells were removed from the flask and washed by centrifugation in RPMI+10% HIFCS+glutamax. The cells were then resuspended at 2×10+7 cells/ml in fresh medium (RPMI+10% HIFCS+glutamax) to which was added calcein-AM (5 gl of stock solution to 1 ml to give a final concentration of 5×10$^{-6}$M). After gentle mixing the cells were incubated at 37° C. in a CO$_2$ incubator for 30 minutes. The cells were then diluted to 50 ml with medium and washed twice by centrifugation at 400×g. Labelled cells were then resuspended at a cell concentration of 1×10+7 cells/ml and incubated with an equal volume of MIP-1α antagonist (10$^{-10}$M to 10$^{-6}$M final concentration) for 30 minutes at 37° C. in a humidified CO$_2$ incubator.

Chemotaxis was performed using Neuroprobe 96-well chemotaxis plates employing 8 µm filters (cat no. 101-8). Thirty microlitres of chemoattractant supplemented with various concentrations of antagonists or vehicle were added to the lower wells of the plate in triplicate. The filter was then carefully positioned on top and then 25 µl of cells preincubated with the corresponding concentration of antagonist or vehicle were added to the surface of the filter. The plate was then incubated for 2 hours at 37° C. in a humidified CO$_2$ incubator. The cells remaining on the surface were then removed by adsorption and the whole plate was centrifuged at 2000 rpm for 10 minutes. The filter was then removed and the cells that had migrated to the lower wells were quantified by the fluorescence of cell associated calcein-AM. Cell migration was then expressed in fluorescence units after subtraction of the reagent blank and values were standardized to % migration by comparing the fluorescence values with that of a known number of labelled cells. The effect of antagonists was calculated as % inhibition when the number of migrated cells were compared with vehicle.

What is claimed is:

1. A compound of general formula

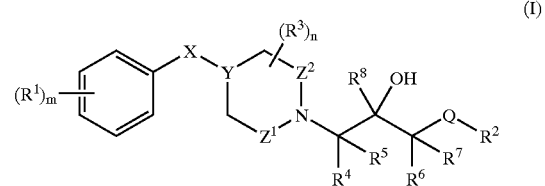

(I)

wherein:

m is 0, 1, 2 or 3;

each R$^1$ independently represents halogen, cyano, nitro, carboxyl, hydroxyl, C$_3$–C$_6$ cycloalkyl, C$_1$–C$_6$ alkoxy, C$_1$–C$_6$ alkoxycarbonyl, C$_1$–C$_6$ haloalkyl, C$_1$–C$_6$ haloalkoxy, —NR$^9$R$^{10}$, C$_3$–C$_6$ cycloalkylamino, C$_1$–C$_6$ alkylthio, C$_1$–C$_6$ alkylcarbonyl, C$_1$–C$_6$ alkylcarbonylamino, sulphonamido, C$_1$–C$_6$ alkylsulphonyl, —C(O)NR$^{11}$R$^{12}$, —NR$^{13}$C(O)—(NH)$_p$R$^{14}$, phenyl, or C$_1$–C$_6$ alkyl optionally substituted by carboxyl or C$_1$–C$_6$ alkoxycarbonyl;

p is 0 or 1;

X represents an oxygen atom or a CH$_2$, OCH$_2$, CH$_2$O, CH$_2$NH, NH, carbonyl or sulphonyl group and Y represents a CH or C(OH) group, provided that when X represents an oxygen atom or a CH$_2$O, CH$_2$NH or NH group, then Y represents a CH group;

Z$^1$ represents a bond or a group (CH$_2$)$_q$ where q is 1;

Z$^2$ represents a bond or a group CH$_2$, with the proviso that Z$^1$ and Z$^2$ do not both simultaneously represent a bond, and wherein Z$^1$ and Z$^2$ do not simultaneously represent CH$_2$;

Q represents an oxygen or sulphur atom or a group CH$_2$ or NH;

R$^2$ represents a group

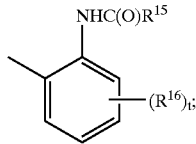

n is 0, 1 or 2;

each R$^3$ independently represents a C$_1$–C$_6$ alkyl, C$_1$–C$_6$ alkoxycarbonyl, —CH$_2$OH or carboxyl group;

R$^4$, R$^5$, R$^6$ and R$^7$ each independently represent a hydrogen atom or a C$_1$–C$_6$ alkyl group, or R$^4$, R$^5$, R$^6$ and R$^7$ together represent a C$_1$–C$_4$ alkylene chain linking the two carbon atoms to which they are attached to form a 4- to 7-membered saturated carbocycle, or R$^5$, R$^6$ and R$^7$ each represent a hydrogen atom and R$^4$ and R$^8$ together with the carbon atoms to which they are attached form a 5- to 6-membered saturated carbocycle;

R$^8$ represents a hydrogen atom, a C$_1$–C$_6$ alkyl group or is linked to R$^4$ as defined above;

R$^9$ and R$^{10}$ each independently represent a hydrogen atom or a C$_1$–C$_6$ alkyl group, or R$^9$ and R$^{10}$ together with the nitrogen atom to which they are attached form a 4- to 7-membered saturated heterocycle;

R$^{11}$ and R$^{12}$ each independently represent a hydrogen atom or a C$_1$–C$_6$ alkyl group optionally substituted by C$_1$–C$_6$ alkoxycarbonyl;

R$^{13}$ represents a hydrogen atom or a C$_1$–C$_6$ alkyl group;

R$^{14}$ represents a hydrogen atom, or a C$_1$–C$_6$ alkyl group optionally substituted by carboxyl, C$_1$–C$_6$ alkoxy or C$_1$–C$_6$ alkoxycarbonyl;

R$^{15}$ represents a group C$_2$–C$_6$ alkyl, C$_2$–C$_6$ alkenyl, C$_3$–C$_6$ cycloalkyl, C$_5$–C$_6$ cycloalkenyl, adamantyl, phenyl or a saturated or unsaturated 5- to 10-membered heterocyclic ring system comprising at least one heteroatom selected from nitrogen, oxygen and sulphur, wherein each group may be optionally substituted by one or more substituents independently selected from nitro, hydroxyl, oxo, halogen, carboxyl, C$_1$–C$_6$ alkyl, C$_1$–C$_6$ alkoxy, C$_1$–C$_6$ alkylthio, C$_1$–C$_6$ alkylcarbonyl, C$_1$–C$_6$ alkoxycarbonyl, phenyl and —NHC(O)—R$^{17}$, with the proviso that R$^{15}$ does not represent an unsubstituted 1-pyrrolidinyl, an unsubstituted 1-piperidinyl or an unsubstituted 1-hexamethyleneiminyl group;

t is 0, 1, 2 or 3;

each R$^{16}$ independently represents halogen, cyano, nitro, carboxyl, hydroxyl, C$_3$–C$_6$ cycloalkyl, C$_1$–C$_6$ alkoxy, C$_1$–C$_6$ alkoxycarbonyl, C$_1$–C$_6$ haloalkyl, C$_1$–C$_6$ haloalkoxy, —NR$^{18}$R$^{19}$, C$_3$–C$_6$ cycloalkylamino, C$_1$–C$_6$ alkylthio, C$_1$–C$_6$ alkylcarbonyl, C$_1$–C$_6$ alkylcarbonylamino, sulphonamido (—SO$_2$NH$_2$), C$_1$–C$_6$ alkylsulphonyl, —C(O)NR$^{20}$R$^{21}$, —NR$^{22}$C(O)(NH)$_v$R$^{23}$, phenyl, or C$_1$–C$_6$ alkyl optionally substituted by carboxyl or C$_1$–C$_6$ alkoxycarbonyl;

R$^{17}$ represents a C$_1$–C$_6$ alkyl, amino or phenyl group;

R$^{18}$ and R$^{19}$ each independently represent a hydrogen atom or a C$_1$–C$_6$ alkyl group, or R$^{18}$ and R$^{19}$ together with the nitrogen atom to which they are attached form a 4- to 7-membered saturated heterocycle;

R$^{20}$ and R$^{21}$ each independently represent a hydrogen atom or a C$_1$–C$_6$ alkyl group optionally substituted by C$_1$–C$_6$ alkoxycarbonyl;

v is 0 or 1;

R$^{22}$ represents a hydrogen atom or a C$_1$–C$_6$ alkyl group; and

R$^{23}$ represents a hydrogen atom, or a C$_1$–C$_6$ alkyl group optionally substituted by carboxyl, C$_1$–C$_6$ alkoxy or C$_1$–C$_6$ alkoxycarbonyl; or a pharmaceutically acceptable salt or solvate thereof.

2. A compound according to claim 1, wherein X represents an oxygen atom or a CH$_2$ or NH group.

3. A compound according to claim 1, wherein Y represents a CH group.

4. A compound according to any one of claim 1, wherein Q represents an oxygen atom.

5. A compound according to claim 1, wherein R$^{15}$ represents a group C$_2$–C$_5$ alkyl, C$_2$–C$_4$ alkenyl, C$_3$–C$_6$ cycloalkyl, C$_5$–C$_6$ cycloalkenyl, adamantyl, phenyl or a saturated or unsaturated 5- to 10-membered heterocyclic ring system comprising at least one heteroatom selected from nitrogen, oxygen and sulphur, wherein each group may be optionally substituted by one, two or three substituents independently selected from hydroxyl, oxo, halogen, carboxyl, C1–C$_6$ alkyl, C$_1$–C$_6$ alkoxy, C$_1$–C$_6$ alkylthio, C$_1$–C$_6$ alkylcarbonyl, C$_1$–C$_6$ alkoxycarbonyl, phenyl and —NHC(O)—R$^{17}$.

6. A compound according to claim 5, wherein the saturated or unsaturated 5- to 10-membered heterocyclic ring system comprising at least one heteroatom selected from nitrogen, oxygen and sulphur, is pyrrolidinyl, piperidinyl, pyrazolyl, thiazolidinyl, thienyl, thiadiazolyl, isoxazolyl, pyrrolyl, furanyl, thiazolyl, indolyl, quinolinyl, benzimidazolyl, triazolyl, tetrazolyl or pyridinyl.

7. A compound according to claim 1, wherein each R$^{16}$ independently represents halogen, cyano, C$_1$–C$_4$ alkoxy, C$_1$–C$_4$ alkoxycarbonyl, C$_1$–C$_4$ haloalkyl, C$_1$–C$_4$ alkylcarbonyl, phenyl or C$_1$–C$_4$ alkyl.

8. A compound of formula (I), or a pharmaceutically acceptable salt or solvate thereof, as defined in claim 1 being selected from:

N-(5-Chloro-2-{3-[3-(4-chloro-phenoxy)-pyrrolidin-1-yl]-2-hydroxy-propoxy}-phenyl)-isobutyramide, Thiophene-2-carboxylic acid (2-{3-[3-(4-chloro-phenoxy)-pyrrolidin-1-yl]-2-hydroxy-propoxy}-phenyl)-amide, N-[(2-{3-[3-(4-Chloro-phenoxy)-pyrrolidin-1-yl]-2-hydroxy-propoxy}-phenylcarbamoyl)-methyl] banzamide, -be Pyrazine-2-carboxylic acid (2-{3-[3-(4-chloro-phenoxy)-pyrrolidin-1-yl]-2-hydroxy-propoxy}-phenyl)-amide, Cyclohexanecarboxylic acid (2-{3-[3-(4-chloro-phenoxy)-pyrrolidin-1-yl]-2-hydroxy-propoxy}-phenyl)-amide, N-(2-{3-[3-(4-Chloro-phenoxy)-pyrrolidin-1-yl]-2-hydroxy-propoxy}-phenyl)-phthalamic acid methyl ester, N-(2-{3-[3-(4-Chloro-phenoxy)-pyrrolidin-1-yl]-2-hydroxy-propoxy}-phenyl)-3-hydroxy-butyramide, N-(2-{3-[3-(4-Chloro-phenoxy)-pyrrolidin-1-yl]-2-hydroxy-propoxy}-phenyl)-2-ureido-acetamide, 4-Acetylamino-N-(2-{3-[3-(4-chloro-phenoxy)-pyrrolidin-1-yl]-2-hydroxy-propoxy}-phenyl)-butyramide, 1-Acetyl-piperidine-4-carboxylic acid (2-{3-[3-(4-chloro-phenoxy)-pyrrolidin-1-yl]-2-hydroxy-propoxy}-phenyl)-amide, N-(2-{3-[3-(4-Chloro-phenoxy)-pyrrolidin-1-yl]-2-hydroxy-propoxy}-phenyl)-3-methoxy-benzamide, 2-Acetylamino-N-(2-{3-[3-(4-chloro-phenoxy)-pyrrolidin-1-yl]-2-hydroxy-propoxy}-phenyl)-3-methyl-butyramide, 2-Acetylamino-N-(2-{3-[3-(4-chloro-phenoxy)-pyrrolidin-1-yl]-2-hydroxy-propoxy}-phenyl)-3-hydroxy-butyramide, Adamantane-1-carboxylic acid (2-{3-[3-(4-chloro-phenoxy)-pyrrolidin-1-yl]-2-hydroxy-propoxy}-phenyl)-amide, 2-Acetylamino-N-(2-{3-[3-(4-chloro-phenoxy)-pyrrolidin-1-yl]-2-hydroxy-propoxy}-phenyl)-3-phenyl-propionamide, N-(2-{3-[3-(4-Chloro-phenoxy)-pyrrolidin-1-yl]-2-hydroxy-propoxy}-phenyl)-2-methoxy-benzamide, 5-Methyl-thiophene-2-carboxylic acid (2-{3-[3-(4-chloro-phenoxy)-pyrrolidin-1-yl]-2-hydroxy-propoxy}-phenyl)-amide, 1-Acetyl-pyrrolidine-2-carboxylic acid (2-{3-[3-(4-chloro-phenoxy)-pyrrolidin-1-yl]-2-hydroxy-propoxy}-phenyl)-amide, 1,5-Dimethyl-1H-pyrazole-3-carboxylic acid (2-{3-[3-(4-chloro-phenoxy)-pyrrolidin-1-yl]-2-hydroxy-propoxy}-phenyl)-amide, 5-Oxo-pyrrolidine-2-carboxylic acid (2-{3-[3-(4-chloro-phenoxy)-pyrrolidin-1-yl]-2-hydroxy-propoxy}-phenyl)-amide, 1H-Indole-6-carboxylic acid (2-{3-[3-(4-chloro-phenoxy)-pyrrolidin-1-yl]-2-hydroxy-propoxy}-phenyl)-amide, Cyclobutanecarboxylic acid (2-{3-[3-(4-chloro-phenoxy)-pyrrolidin-1-yl]-2-hydroxy-propoxy}-phenyl)-amide, N-(2-{3-[3-(4-Chloro-phenoxy)-pyrrolidin-1-yl]-2-hydroxy-propoxy}-phenyl)-propionamide, Pentanoic acid (2-{3-[3-(4-chloro-phenoxy)-pyrrolidin-1-yl]-2-hydroxy-propoxy}-phenyl)-amide, Pent-4-enoic acid (2-{3-[3-(4-chloro-phenoxy)-pyrrolidin-1-yl]-2-hydroxy-propoxy}-phenyl)-amide, Cyclopentanecarboxylic acid (2-{3-[3-(4-chloro-phenoxy)-pyrrolidin-1-yl]-2-hydroxy-propoxy}-phenyl)-amide, Cyclopropanecarboxylic acid (2-{3-[3-(4-chloro-phenoxy)-pyrrolidin-1-yl]-2-hydroxy-propoxy}-phenyl)-amide, N-(2-{3-[3-(4-Chloro-phenoxy)-pyrrolidin-1-yl]-2-hydroxy-propoxy}-phenyl)-isobutyramide, N-(2-{3-[3-(4-Chloro-phenoxy)-pyrrolidin-1-yl]-2-hydroxy-propoxy}-phenyl)-2-methylsulfanyl-acetamide, 2-Acetylamino-N-(2-{3-[3-(4-chloro-phenoxy)-pyrrolidin-1-yl]-2-hydroxy-propoxy}-phenyl)-propionamide, N-(2-{3-[3-(4-Chloro-phenoxy)-pyrrolidin-1-yl]-2-hydroxy-propoxy}-phenyl)-butyramide, N-(2-{3-[3-(4-Chloro-phenoxy)-pyrrolidin-1-yl]-2-hydroxy-propoxy}-phenyl)-3-methyl-butyramide, N-(2-{3-[3-(4-Chloro-phenoxy)-pyrrolidin-1-yl]-2-hydroxy-propoxy}-phenyl)-2-methoxy-acetamide, N-(2-{3-[3-(4-Chloro-phenoxy)-pyrrolidin-1-yl]-2-hydroxy-propoxy}-phenyl)-2,2-dimethyl-propionamide, 5-Oxo-hexanoic acid (2-{3-[3-(4-chloro-phenoxy)-pyrrolidin-1-yl]-2-hydroxy-propoxy}-phenyl)-amide, 2-Chloro-N-(2-{3-[3-(4-chloro-phenoxy)-pyrrolidin-1-yl]-2-hydroxy-propoxy}-phenyl)-benzamide, 3-Chloro-N-(2-{3-[3-(4-chloro-phenoxy)-pyrrolidin-1-yl]-2-hydroxy-propoxy}-phenyl)-benzamide, (4R)-N-(2-{3-[3-(4-chlorophenoxy)-1-pyrrolidinyl]-2-hydroxypropoxy}phenyl)-1,3-thiazolidine-4-carboxamide ditrifluoroacetate, N-(2-{3-[3-(4-chlorophenoxy)-1-pyrrolidinyl]-2-hydroxypropoxy}phenyl)-2,2,2-trifluoroacetamide hydrochloride, Furan-2-carboxylic acid (2-{3-[3-(4-chloro-phenoxy)-pyrrolidin-1-yl]-2-hydroxy-propoxy}-4-methyl-phenyl)-amide, 1H-Pyrrole-2-carboxylic acid (2-{3-[3-(4-chloro-phenoxy)-pyrrolidin-1-yl]-2-hydroxy-propoxy}-4-methyl-phenyl)-amide, Thiophene-2-carboxylic acid (2-{3-[3-(4-chloro-phenoxy)-pyrrolidin-1-yl]-2-hydroxy-propoxy}-4-methyl-phenyl)-amide, Cyclopentanecarboxylic acid (2-{3-[3-(4-chloro-phenoxy)-pyrrolidin-1-yl]-2-hydroxy-propoxy}-4-methyl-phenyl)-amide, 5-Methyl-thiophene-2-carboxylic acid (2-{3-[3-(4-chloro-phenoxy)-pyrrolidin-1-yl]-2-hydroxy-propoxy}-4-methyl-phenyl)-amide, 3-Chloro-thiophene-2-carboxylic acid (2-{3-[3-(4-chloro-phenoxy)-pyrrolidin-1-yl]-2-hydroxy-propoxy}-4-methyl-phenyl)-amide, 5-Methyl-isoxazole-4-carboxylic acid (2-{3-[3-(4-chloro-phenoxy)-pyrrolidin-1-yl]-2-hydroxy-propoxy}-4-methyl-phenyl)-amide,

[1,2,3]Thiadiazole-4-carboxylic acid (2-{3-[3-(4-chloro-phenoxy)-pyrrolidin-1-yl]-2-hydroxy-propoxy}-4-methyl-phenyl)-amide, 3-Methyl-furan-2-carboxylic acid (2-{3-[3-(4-chloro-phenoxy)-pyrrolidin-1-yl]-2-hydroxy-propoxy}-4-methyl-phenyl)-amide, Cyclopent-1-enecarboxylic acid (2-{3-[3-(4-chloro-phenoxy)-pyrrolidin-1-yl]-2-hydroxy-propoxy}-4-methyl-phenyl)-amide, 2-Methyl-furan-3-carboxylic acid (2-{3-[3-(4-chloro-phenoxy)-pyrrolidin-1-yl]-2-hydroxy-propoxy}-4-methyl-phenyl)-amide, 3-Methyl-thiophene-2-carboxylic acid (2-{3-[4-(3,4-dichloro-phenoxy)-piperidin-1-yl]-2-hydroxy-propoxy}-phenyl)-amide, 5-Nitro-1H-pyrazole-3-carboxylic acid (2-{3-[3-(4-chloro-phenoxy)-pyrrolidin-1-yl]-2-hydroxy-propoxy}-4-methyl-phenyl)-amide, Thiophene-3-carboxylic acid (2-{3-[3-(4-chloro-phenoxy)-pyrrolidin-1-yl]-2-hydroxy-propoxy}-4-methyl-phenyl)-amide, Cyclobutanecarboxylic acid (2-{3-[3-(4-chloro-phenoxy)-pyrrolidin-1-yl]-2-hydroxy-propoxy}-4-methyl-phenyl)-amide, Furan-2-carboxylic acid (2-{3-[3-(4-fluoro-phenoxy)-pyrrolidin-1-yl]-2-hydroxy-1-propoxy}-4-methyl-phenyl)-amide, 1H-Pyrrole-2-carboxylic acid (2-{3-[3-(4-fluoro-phenoxy)-pyrrolidin-1-yl]-2-hydroxy-propoxy}-4-methyl-phenyl)-amide, Thiophene-2-carboxylic acid (2-{3-[3-(4-fluoro-phenoxy)-pyrrolidin-1-yl]-2-hydroxy-propoxy}-4-methyl-phenyl)-amide, 3-Chloro-thiophene-2-carboxylic acid (2-{3-[3-(4-fluoro-phenoxy)-pyrrolidin-1-yl]-2-hydroxy-propoxy}-4-methyl-phenyl)-amide, 5-Methyl-isoxazole-4-carboxylic acid (2-{3-[3-(4-fluoro-phenoxy)-pyrrolidin-1-yl]-2-hydroxy-propoxy}-4-methyl-phenyl)-amide, 3-Methyl-furan-2-carboxylic acid (2-{3-[3-(4-fluoro-phenoxy)-pyrrolidin-1-yl]-2-hydroxy-propoxy}-4-methyl-phenyl)-amide, Cyclopent-1-enecarboxylic acid (2-{3-[3-(4-fluoro-phenoxy)-pyrrolidin-1-yl]-2-hydroxy-propoxy}-4-methyl-phenyl)-amide, 2-Methyl-furan-3-carboxylic acid (2-{3-[3-(4-fluoro-phenoxy)-pyrrolidin-1-yl]-2-hydroxy-propoxy}-4-methyl-phenyl)-amide, 3-Methyl-thiophene-2-carboxylic acid (2-{3-[3-(4-fluoro-phenoxy)-pyrrolidin-1-yl]-2-hydroxy-propoxy}-4-methyl-phenyl)-amide, 5-Chloro-thiophene-2-carboxylic acid (2-{3-[3-(4-fluoro-phenoxy)-pyrrolidin-1-yl]-2-hydroxy-propoxy}4-methyl-phenyl)-amide, Thiophene-3-carboxylic acid (2-{3-[3-(4-fluoro-phenoxy)-pyrrolidin-1-yl]-2-hydroxy-propoxy}-4-methyl-phenyl)-amide, 2,5-Dimethyl-furan-3-carboxylic acid (2-{3-[3-(4-fluoro-phenoxy)-pyrrolidin-1-yl]-2-hydroxy-propoxy}-4-methyl-phenyl])-amide, Cyclobutanecarboxylic acid (2-{3-[3-(4-fluoro-phenoxy)-pyrrolidin-1-yl]-2-hydroxy-propoxy}-4-methyl-phenyl)-amide, Furan-3-carboxylic acid (2-{3-[3-(4-fluoro-phenoxy)-pyrrolidin-1-yl]-2-hydroxy-propoxy}-4-methyl-phenyl)-amide, N-{2-[(3-{3-[(4-fluorophenyl)oxy]-1-pyrrolidinyl}-2-hydroxypropyl)oxy]-4-methylphenyl}-1H-pyrrole-2-carboxamide, N-{2-[(3-{3-[(4-chlorophenyl)oxy]-1-pyrrolidinyl}-2-hydroxypropyl)oxy]-4-methylphenyl}-3-thiophenecarboxamide, N-{2-[(3-{3-[(4-chlorophenyl)oxy]-1-pyrrolidinyl}-2-hydroxy-2-methylpropyl)oxy]phenyl}-2-thiophenecarboxamide, compound with trifluoroacetic acid, N-{2-[(3-{3-[(4-fluorophenyl)oxy]-1-pyrrolidinyl}-2-hydroxypropyl)oxy]-4-methylphenyl}-2-thiophenecarboxamide, N-{2-[(3-{3-[(4-chlorophenyl)oxy]-1-pyrrolidinyl}-2-hydroxypropyl)oxy]phenyl}-2-furancarboxamide, N-{2-[(3-{3-[(4-chlorophenyl)oxy]-1-pyrrolidinyl}-2-hydroxypropyl)oxy]phenyl}-1-pyrrole-2-carboxamide N-{2-[(3-{3-[(4-chlorophenyl)oxy]-1-pyrrolidinyl)}-2-hydroxypropyl)oxy]-4-methylphenyl}-1H-pyrrole-3-carboxamide,.

N-{2-[(3-{3-[(4-fluorophenyl)oxy]-1-pyrrolidinyl)}-2-hydroxypropyl)oxy]-4-methylphenyl}-2-furancarboxamide, N-{2-[(3-{3-[(4-chlorophenyl)oxy]-1-pyrrolidinyl)}-2-hydroxy-2-methylpropyl)oxy] phenyl}cyclopentanecarboxamide, compound with trifluoracetic acid, N-(2-{3-[3-(4-Fluoro-phenoxy)-pyrrolidin-1-yl]-2-hydroxy-2-methyl-propoxy}-phenyl)-benzamide, N-(2-{3-[3-(4-Cyano-phenoxy)-pyrrolidin-1-yl]-2-hydroxy-2-methyl-propoxy}-phenyl)-benzamide, and N-(2-{3-[3-(4-Chloro-phenoxy)-pyrrolidin-1-yl]-2-hydroxy-2-methyl-propoxy}-phenyl)-benzamide.

9. A process for the preparation of a compound of formula (I) as defined in claim 1 which comprises reacting a compound of general formula

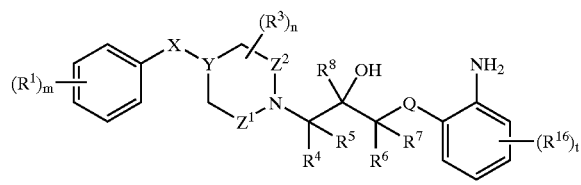

or a salt thereof, wherein m, n, t, $R^1$, $R^3$, $R^4$, $R^5$, $R^6$, $R^7$, $R^8$, $R^{16}$, Y, Q, $Z^1$ and $Z^2$ are as defined in claim 1, with a compound of general formula $$R^{15}-CO_2H \quad (III)$$

or chemically equivalent derivative thereof, wherein $R^{15}$ is as defined in claim 1;

and optionally thereafter forming a pharmaceutically acceptable salt or solvate of the compound of formula (I) obtained.

10. A pharmaceutical composition comprising a therapeutically effective amount of a compound of formula (I), or a pharmaceutically acceptable salt or solvate thereof, as claimed in claim 1 in association with a pharmaceutically acceptable adjuvant, diluent or carrier.

11. A process for the preparation of a pharmaceutical composition, the process comprising mixing a therapeutically effective amount of a compound of formula (I), or a pharmaceutically acceptable salt or solvate thereof, as claimed in claim 1 with a pharmaceutically acceptable adjuvant, diluent or carrier.

* * * * *